(12) United States Patent
Silverman et al.

(10) Patent No.: US 6,468,983 B2
(45) Date of Patent: *Oct. 22, 2002

(54) RNASE L ACTIVATORS AND ANTISENSE OLIGONUCLEOTIDES EFFECTIVE TO TREAT TELOMERASE-EXPRESSING MALIGNANCIES

(75) Inventors: Robert H. Silverman, Beachwood, OH (US); Seiji Kondo, Shaker Heights, OH (US); John K. Cowell, Shaker Heights, OH (US); Guiying Li, Branford, CT (US); Paul F. Torrence, Silver Spring, MD (US)

(73) Assignees: The Cleveland Clinic Foundation, Cleveland, OH (US); The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/018,125

(22) Filed: Feb. 3, 1998

(65) Prior Publication Data

US 2001/0007902 A1 Jul. 12, 2001

Related U.S. Application Data

(60) Provisional application No. 60/044,507, filed on Apr. 21, 1997.

(51) Int. Cl.$^7$ ............................ A61K 48/00; L07H 21/04
(52) U.S. Cl. .............................. 514/44; 435/6; 435/455; 435/375; 435/377; 536/23.1; 536/24.1; 536/24.5; 536/25.2
(58) Field of Search ............................ 435/6, 455, 375, 435/377; 536/23.1, 24.1, 24.31, 24.5, 25.2; 514/44

(56) References Cited

U.S. PATENT DOCUMENTS 5,525,468 A * 6/1996 McSwiggen 5,583,032 A * 12/1996 Torrence et al. ......... 435/240.2
5,776,679 A * 7/1998 Villeponteau et al. ......... 435/6

OTHER PUBLICATIONS

Shigehiko Mukai et al., Cancer Research, 60, pp. 4461–4467, Aug. 15, 2000.*
S. Koga et al., Gene Therapy, 2001, 8 pp. 654–658.*
Yasuko Kondo et al., Oncoene, 2000, 19, pp. 2205–2211.*
Seiji Kondo et al., Oncogene, 1998, 16, pp. 3323–3330.*
Seiji Kondo et al., The Faseb Journal, vol. 12, Jul. 1998, pp. 801–811.*
Thierry et al, Overcoming Multidrug Resistance in Human Tumor Cells Using Free and Liposomally Encapsulated Antisense Oligodeoxynucleotides, Feb. 1993, Biochemical and Biophysical Research Communications, vol. 190, No. 3, pp. 952–960.*
Blake et al, Hybridization Arrest of Globin Synthises in Rabbit Reticulocyte Lysates and Cells by Oligodeoxyribonucleoside Methylphonates, 1985, Biochemistry, vol. 24, pp. 6139–6145.*
Golden, F. "Of Mice and Men: Don,t Blame the Rodents" Time, May 18, 1998.*
Branch, A. "A Good Antisense Molecule is Hard to Find" TIBS vol. 23:45–50, Feb. 1998.*
Agrawal, S. "Antisense Oligonucleotides: Towards Clinical Trials" Tibtech vol. 14:376–387, Oct. 1996.*

* cited by examiner

Primary Examiner—Sean McGarry
(74) Attorney, Agent, or Firm—Proskauer Rose LLP; Kristin H. Neuman, Esq.

(57) ABSTRACT

The present invention relates to chimeric molecules comprising an oligonucleotide complementary to a region of the ribonucleotide component of telomerase attached to an activator of RNase L ("activator-antisense complex") which specifically cleaves the ribonucleotide portion of a telomerase enzyme. The present invention relates to methods of inhibiting telomerase enzymatic activity with activator-antisense complexes targeted to the RNA component of telomerase. The present invention further relates to methods of treating malignant neoplastic disease, wherein the malignant cells contain a telomerase activity that is necessary for the growth of the malignant cells.

29 Claims, 18 Drawing Sheets

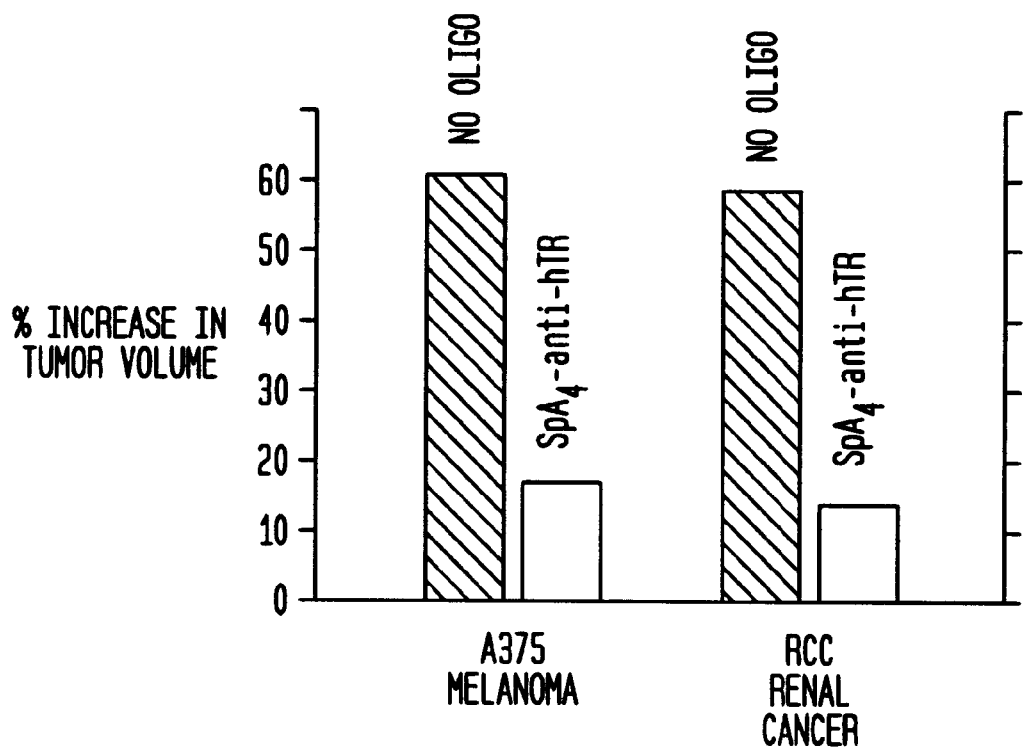

US 6,468,983 B2

Figure 1:
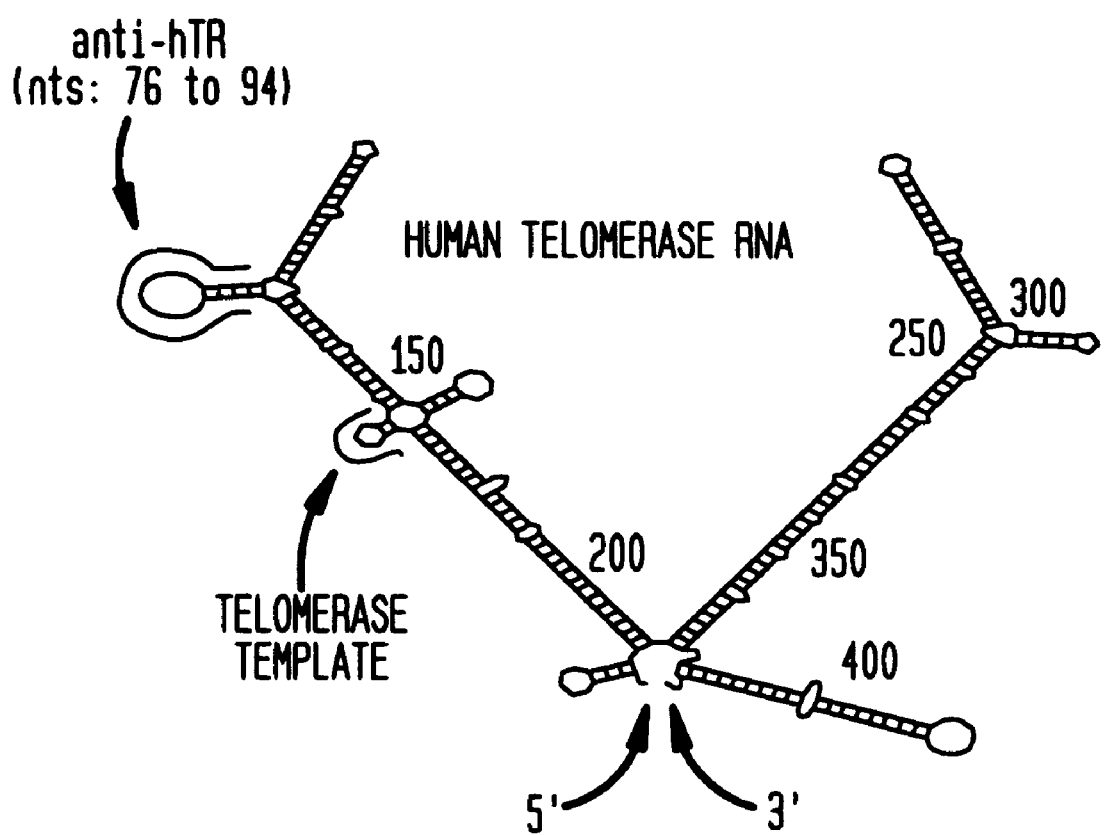

RNASE L ACTIVATORS AND ANTISENSE OLIGONUCLEOTIDES EFFECTIVE TO TREAT TELOMERASE-EXPRESSING MALIGNANCIES

This application claims benefit of U.S. provisional application Ser. No. 60/044,507, filed Apr. 21, 1997, which is incorporated herein in its entirety.

1. INTRODUCTION

The present invention relates to a chimeric molecule comprising an oligonucleotide complementary to some portion of the ribonucleotide component of telomerase and an activator of RNase L ("activator-antisense complexes"). The present invention relates to compounds useful for the treatment of disorders and diseases related to enhanced or elevated telomerase activity. In particular, the present invention relates to compounds and methods of their use for treating humans having a malignant neoplastic disease of the type, wherein the malignant cells contain a telomerase enzyme that is necessary for the continued growth of the tumor. Particularly, the invention concerns a RNase L activator antisense complex that targets the RNA component of telomerase enzymes, cleaves the RNA and inhibits telomerase activity. More particularly, the invention relates to activator-antisense complexes, in which the oligonucleotide is selected to bind to regions of the ribonucleotide component of telomerase that possess repeated or consensus sequences. The invention further relates to activator-antisense complexes, in which the oligonucleotide is selected to bind to a portion of the RNA component that normally has no self-hybridizing secondary structure.

2. BACKGROUND

2.1 ACTIVATOR-ANTISENSE COMPLEXES

Activator-antisense complexes (termed therein "2-5A:AS") have been described previously for use to cleave specifically selected strands of RNA (Torrence et al., 1993, WO 94/09129 by Torrence et al., U.S. Pat. No. 5,583,032). The mechanism of action of activator-antisense complexes is different than the mechanism of action of other antisense oligonucleotides. The activator portion of the activator-antisense complexes activates RNase L and the antisense domain serves as a specific, high affinity binding site for the target RNA. The result is the selective cleavage of the target RNA by RNase L.

Physiologically, RNase L functions as part of the interferon system in restricting virus replication in cells of higher vertebrates (reviewed in Silverman, 1994). Interferon treatment of cells activates genes encoding 2-5A synthetases, double-stranded RNA (dsRNA)-dependent enzymes that produce 5'-triphosphorylated, 2',5'-linked oligoadenylates (2',5'A) from ATP. Viral dsRNAs are potential activators of these enzymes (Gribaudo et al., 1991, J. Virol. 65, 1748). The 2',5'A binds to and activates RNase L resulting in the general cleavage of cellular and viral RNA; thus restricting the replication of some picornaviruses (Chebath et al., 1987, Nature 330, 587; Rysiecki et al., 1989, J. Interferon Res. 9, 649; and Hassel et al., 1994, EMBO J. 12, 3297).

RNase L is not specific for cleaving viral RNA. For instance, in interferon-treated, encephalomyocarditis virus infected cells, RNase L causes degradation of ribosomal RNA (Wreschner et al., 1981, Nucleic Acid Res. 9, 1571). Through the activator-antisense approach, RNase L is converted from a non-specific nuclease to a highly specific endoribonuclease that selectively cleaves mRNA targets. This has been demonstrated in a cell-free system from Daudi cells, a human lymphoblastoid cell line, in which a modified HIV-1 vif mRNA was targeted for cleavage by an activator-antisense complex (Torrence et al., 1993, Proc. Natl. Acad. Sci. USA 90, 1300). Subsequently, purified RNase L has been directed by an activator-antisense complex to cleave selectively an mRNA target encoding the protein kinase PKR in the presence of a nontargeted mRNA (Maran et al., 1994, Science 265, 789). Furthermore, in HeLa cells, the use of activator-antisense complexes, which were directed to a sequence in PKR mRNA, resulted in the ablation of PKR mRNA and enzyme activity (ibid.) such that the dsRNA-mediated activation of transcription factor, NF-kB was ablated. More recently, it was shown that the activation of RNase L by an activator-antisense complex results in the catalytic degradation of PKR mRNA ($k_{cat}$ of about 7 sec$^{-1}$) (Maitra et al., 1995, J. Biol. Chem. 270, 15071).

2.2 TELOMERASE

Telomeres correspond to the ends of eukaryotic chromosomes and are specialized structures containing unique (TTAGGG)$_N$ repeats. (Blackburn, 1991, Nature 350, 569–573). Telomeres protect the chromosomes from DNA degradation, end-to-end fusions, rearrangements, and chromosome loss. (deLange, T., 1994, Proc. Natl. Acad. Sci. 91, 2882–85). Because cellular DNA polymerases cannot replicate the 5' end of the linear DNA molecules found in eukaryotic chromosomes, the number of telomere repeats decreases by 50–200 nucleotides/cell division during aging of normal somatic cells. (Harley, et al., 1990, Nature 345, 458–460; Hastie, et al., 1990, Nature 346, 866–68). Shortening of telomeres may also control the proliferative capacity of normal cells. Telomerase, a ribonucleic acid-protein complex, adds hexameric repeats of 5'-TTAGGG-3' to the end of telomeres to prevent progressive loss. (Greider et al., 1985, Cell 43, 405–413). Although the vast majority of normal somatic cells do not express telomerase, most types of tumor cells express telomerase at high levels. (Kim et al., 1994, Science 266, 2011–15; Broccoli et al., 1995, Proc. Natl. Acad. Sci. 92, 9082–86; Hiyama et al., 1995, J. Natl. Cancer Inst. 87, 895–902; Hiyama et al., 1995, Cancer Res. 55, 3258–62). High levels of telomerase in a tumor are correlated with a poor prognosis thought to be necessary for a cell to become malignant and conversely low levels of telomerase are associated with a favorable prognosis. (Hiyama, supra). Although telomerase-independent mechanisms for telomere maintenance cannot be formally excluded, (Rogan et al., 1995, Mol. Cell. Biol. 15, 4745–53; Strahl et al., 1996, Mol. Cell. Biol. 16, 53–652), telomerase activity is most likely to be the dominant mechanism. (Holt et al., 1996, Mol. Cell. Biol. 16, 2932–39). Thus, telomerase activity is considered to be a necessary factor for the malignant transformation of a cell.

Recently, it has been observed that when HeLa cells were transfected with an plasmid that expresses an mRNA complementary to the RNA component of human telomerase, the transfected cells were found to lose telomeric DNA and to die after 23 to 26 doublings. (Feng et al., 1995, Science 269, 1236–41).

U.S. Pat. No. 5,583,016 Villeponteau ("Villeponteau") discloses the sequence of the RNA component of human telomerase ("hTR"). Villeponteau describes in theory the use of oligonucleotides for the inhibition of telomerase gene expression or oligonucleotides which bind to the RNA component of telomerase and prevent it from acting as a substrate in humans. U.S. Pat. Nos. 5,489,508 and 5,645,986 to West describe both therapeutics and diagnostic assays directed to telomerase, in particular, oligonucleotides which could be designed to bind to a telomerase RNA component, prevent telomerase from binding to a telomere and thereby inhibit telomerase activity. These U.S. patents also describe the use of antisense oligonucleotides to inhibit telomerase gene expression. Those groups have described in theory, methods of inhibiting telemerase activity by targeting the ability of telomerase to extend telomeres or by inhibiting telomerase gene expression.

3. SUMMARY OF THE INVENTION

The present invention relates to chimeric molecules comprising an oligonucleotide complementary to a region of the ribonucleotide component of telomerase attached to an activator of RNase L ("activator-antisense complex") which specifically cleaves the ribonucleotide portion of a telomerase enzyme. The present invention relates to methods of inhibiting telomerase enzymatic activity with activator-antisense complexes targeted to the RNA component of telomerase.

The present invention provides a complex that is useful for the treatment of malignant disease by inhibition of telomerase activity. The essential components of the complex are an antisense oligonucleotide which has a sequence that is complementary to between about 12 and about 25 nucleotides of the RNA component of human telomerase and an activator of RNase L (henceforth, an "anti-telomerase activator-antisense complex"). In a preferred embodiment, the antisense portion of the activator-antisense complex is complementary to 18 or 19 nucleotides of the RNA component of telomerase. The elements of the activator-antisense complex may be covalently or non-covalently linked.

The activator-antisense complexes of the present invention can be transported across the cell membrane without the use of carriers or permeabilizing agents. The activator-antisense complexes of the present invention can also be used with an agent to facilitate transport across a cell membrane, e.g. lipofectamine. Once internalized the activator-antisense complexes lead to the formation of enzyme-antisense complexes, which causes destruction of the telomerase RNA.

The invention is based, in part, on the Applicants' unexpected result that exposure of a human malignant glioma cell to a 2-5A-activator linked to 19-mer antisense oligonucleotide targeted to the RNA component of telomerase (2-5A-hTR) effectively suppressed tumor cell growth and survival in vitro and in vivo. As shown by the Applicants, the dose of 2-5A-hTR required to block proliferation and survival of tumor cells can be reduced by 10-fold using lipofectamine to facilitate cellular uptake of the oligonucleotide. Applicants have found that malignant glioma cells treated with 2-5A-anti-hTR undergo cell death by apoptosis. Applicants have also demonstrated that when 2-5A-anti-hTR was administered in vivo to mice with intracranial implantations of human malignant gliomes, 50% of the mice survived at 62 days post-tumor implantation. The Applicants have further demonstrated that a broad range of cancer cell types are susceptible to the antiproliferative effects of 2-5A-anti-hTR.

The present invention further relates to pharmaceutical compositions comprising the anti-telomerase activator-antisense complexes for the treatment and prevention of cell proliferative disorders related to enhanced telomerase activity, e.g., malignant neoplastic disease. The present invention also relates to methods of treating and preventing cell proliferative disorders, such as cancer, related to enhanced telomerase activity including, but not limited to, brain cancer, breast cancer, prostate cancer, renal cancer and melanoma. In particular, the present invention relates to methods of treating and preventing the growth of tumors, wherein the tumor cells contain a telomerase enzyme that is necessary for the continued growth of the tumor.

4. BRIEF DESCRIPTION OF THE FIGURES

FIG. 1. Predicted MFOLD secondary structure of the human telomerase RNA which has a $\Delta G$ of $-168$ kcal per mole. The positions of the telomerase template (nucleotides 46–56) and the sequence used to design the antisense oligonucleotides (nucleotides 76–94) are indicated by the arrows.

Figure 2:

FIG. 2. Autoradiograph following the TRAP assay using extracts of cultured astrocytes (PIN), low grade astrocytoma (RTLGA), and malignant glioma cells (GB-1, U251-MG, T98G, and U373-MG). Only the glioma cells demonstrate telomerase activity.

Figure 3:
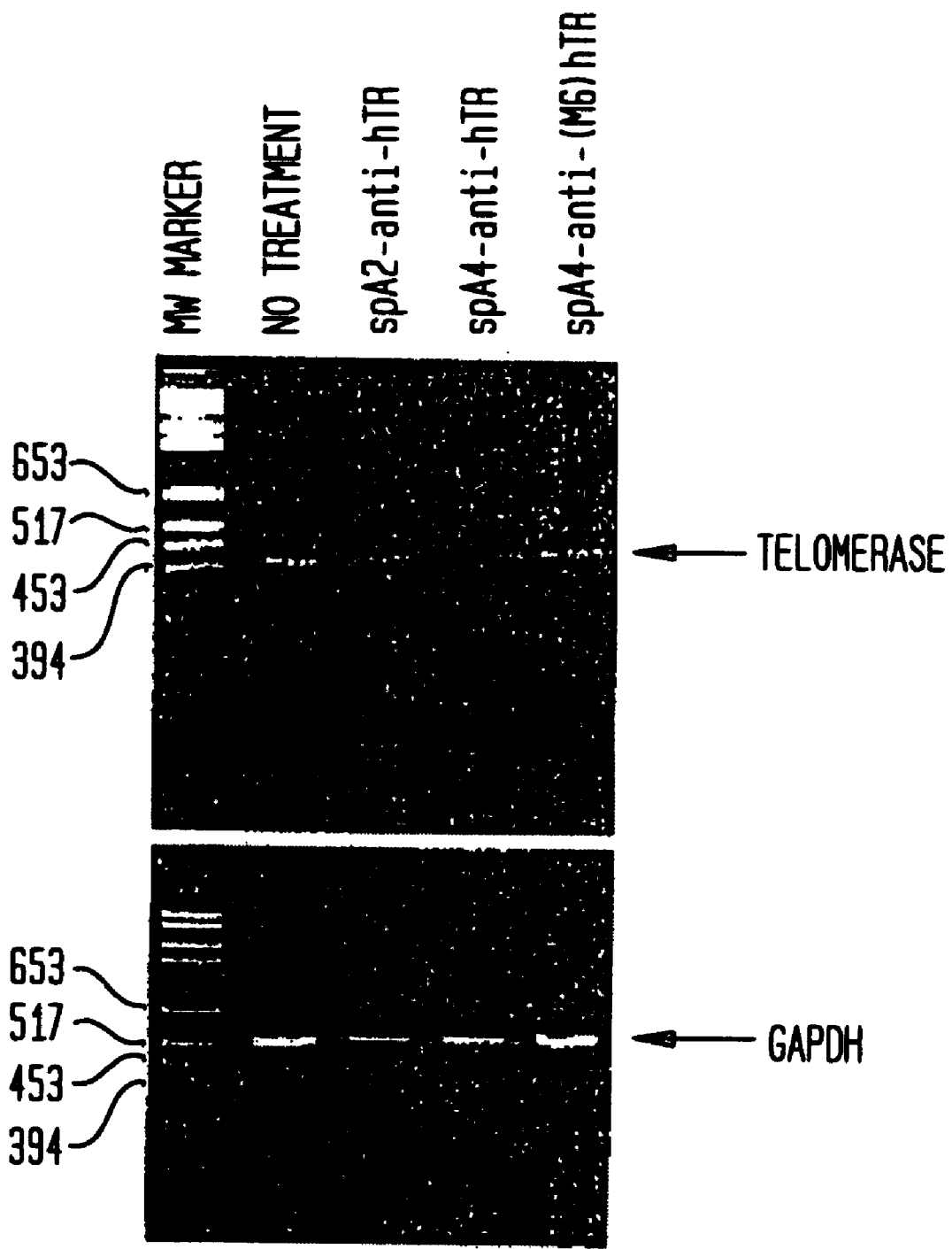

FIG. 3. Effect of $spA_4$-anti-hTR on the expression of telomerase RNA in U251-MG cells. Five hours after oligo treatment, total RNA was isolated and used for RT-PCR in the presence of telomerase or GAPDH specific primers. Reaction products were visualized after 1.2% agarose gel electrophoresis and ethidium bromide staining.

Figure 4:
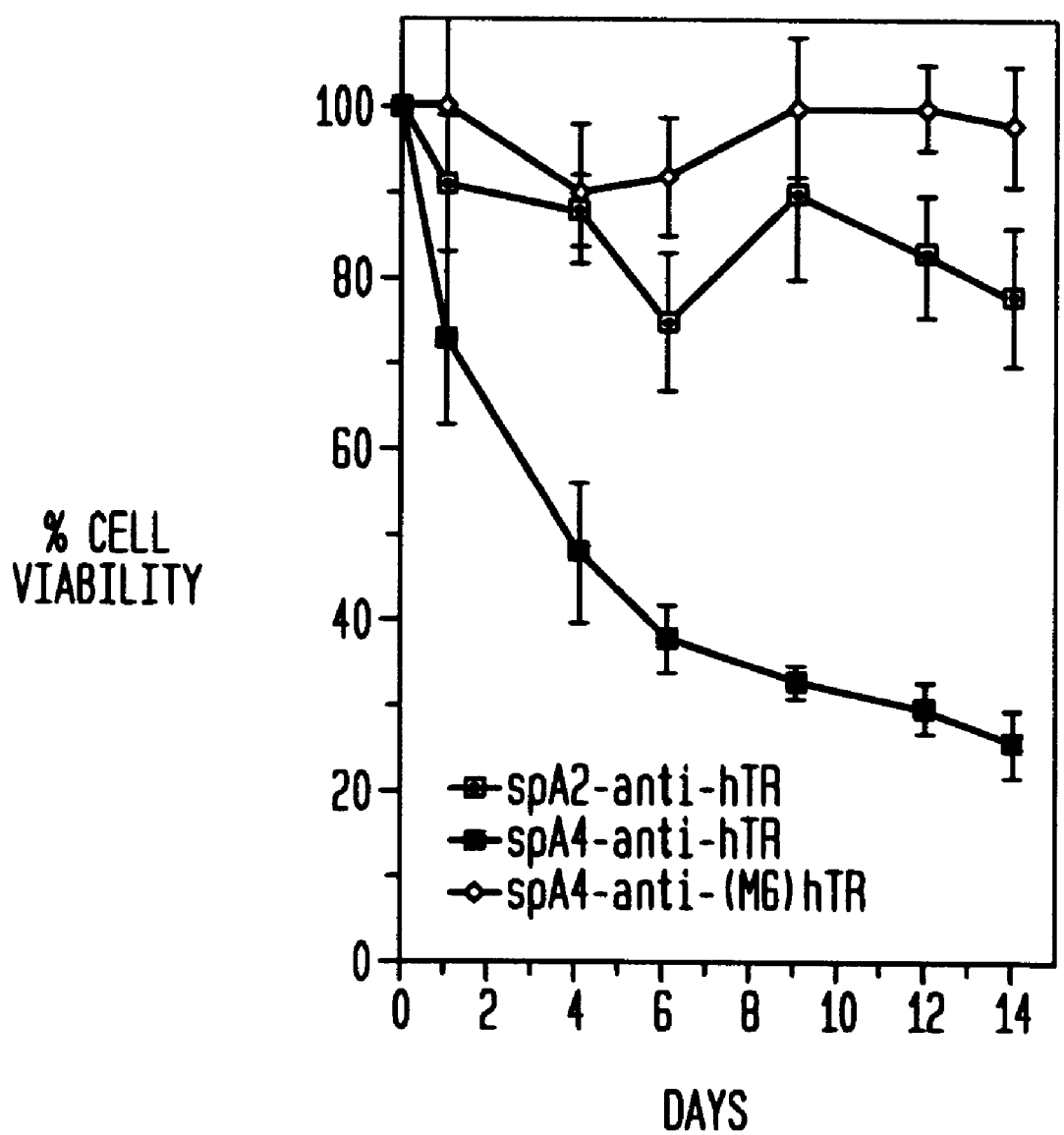

FIG. 4. Effect of $spA_4$-anti-hTR on viability of U251-MG cells. Cells were treated with 2-5A antisense (5 micromolar, every 12 hr) and their viability was determined by trypan blue exclusion. In each treatment group the percentage of viable cells was determined in each of 6 different wells and the values shown on the plot represent the means S.D.

Figure 5:
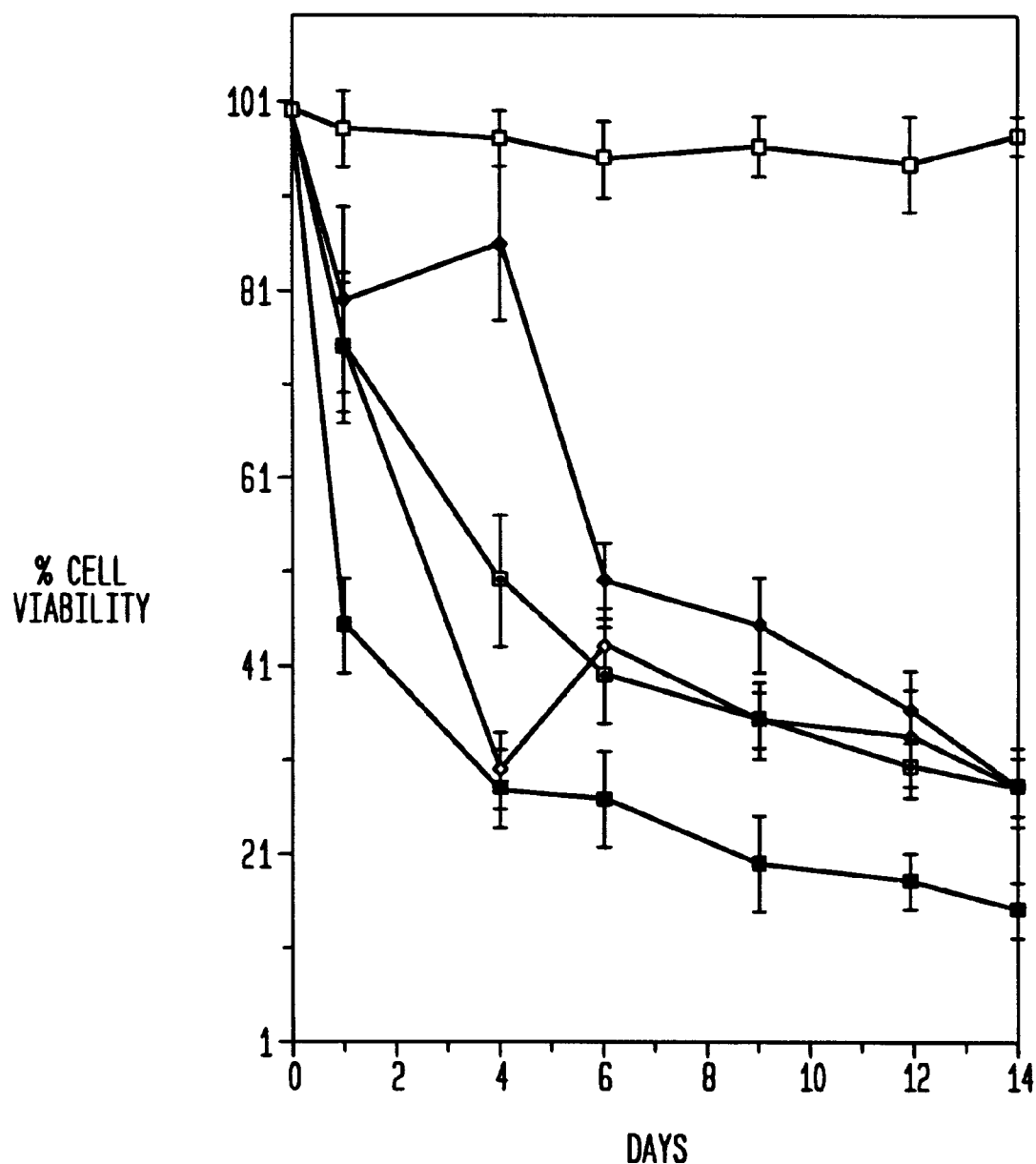

FIG. 5. Comparison of the viability between normal human astrocytes and GBM cell lines treated with $spA_4$-anti-hTR. Over the treatment period the cell viability of the PIN cells was reduced by less than 5% compared with the significant effect seen in the tumor cell lines.

Figure 6:
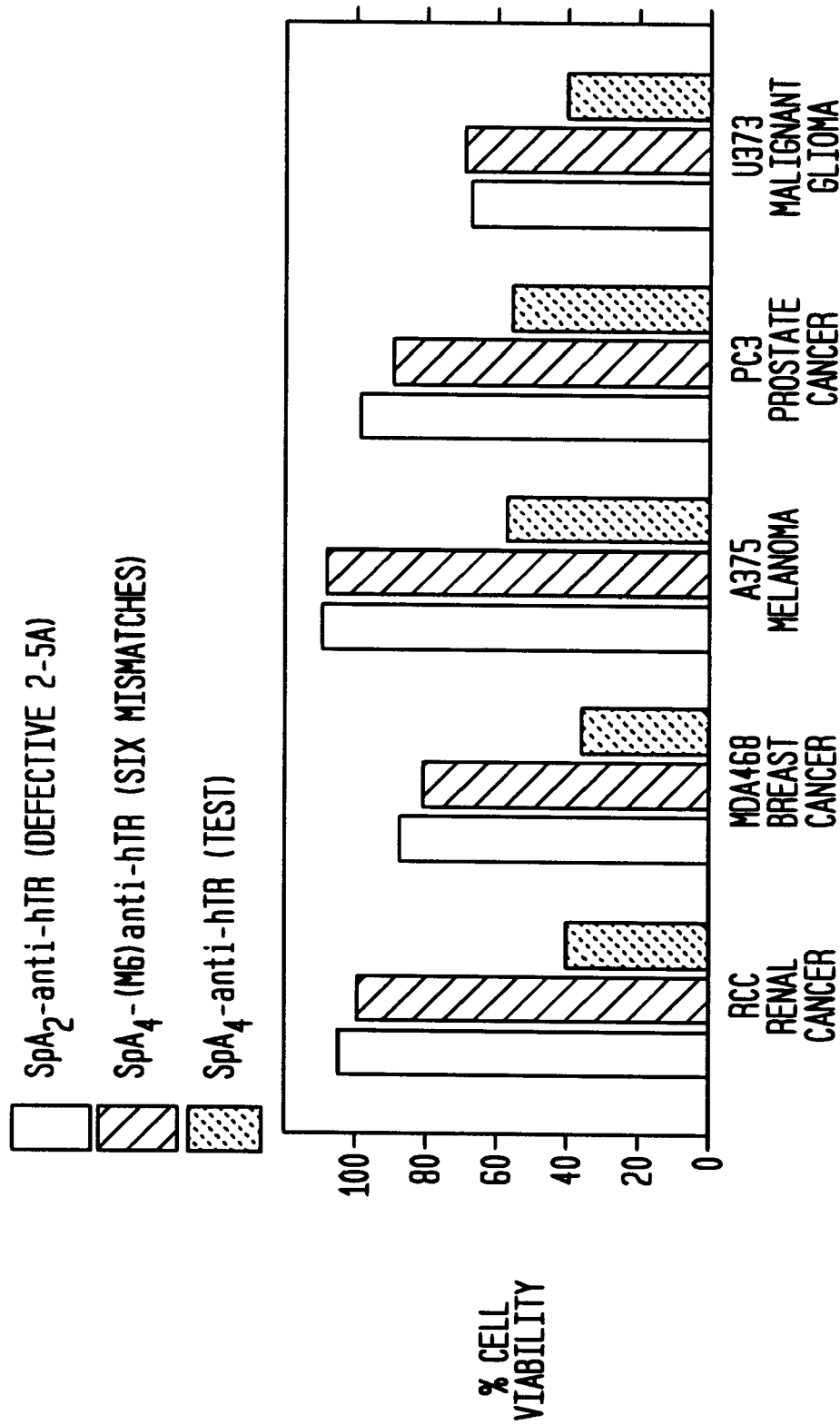

FIG. 6. Bar graph demonstrating the broad antiproliferative effects of $SpA_4$-anti-HTR $SpA_4$-anti-hTR specifically suppressed growth of RCC Renal Cell Carcinoma cells, MDA 468 human breast cancer, A375 human melanoma cells, PC3 human prostate cells and U373 human malignant glioma cells. Cells were treated daily with 0.5 micromolar $SpA_4$-anti-hTR, $SpA_4$-anti(M6)-hTR, $SpA_2$-anti-hTR in the presence of lipofectamine, or with lipofectamine alone. Results are the average of duplicate assays.

Figure 7:
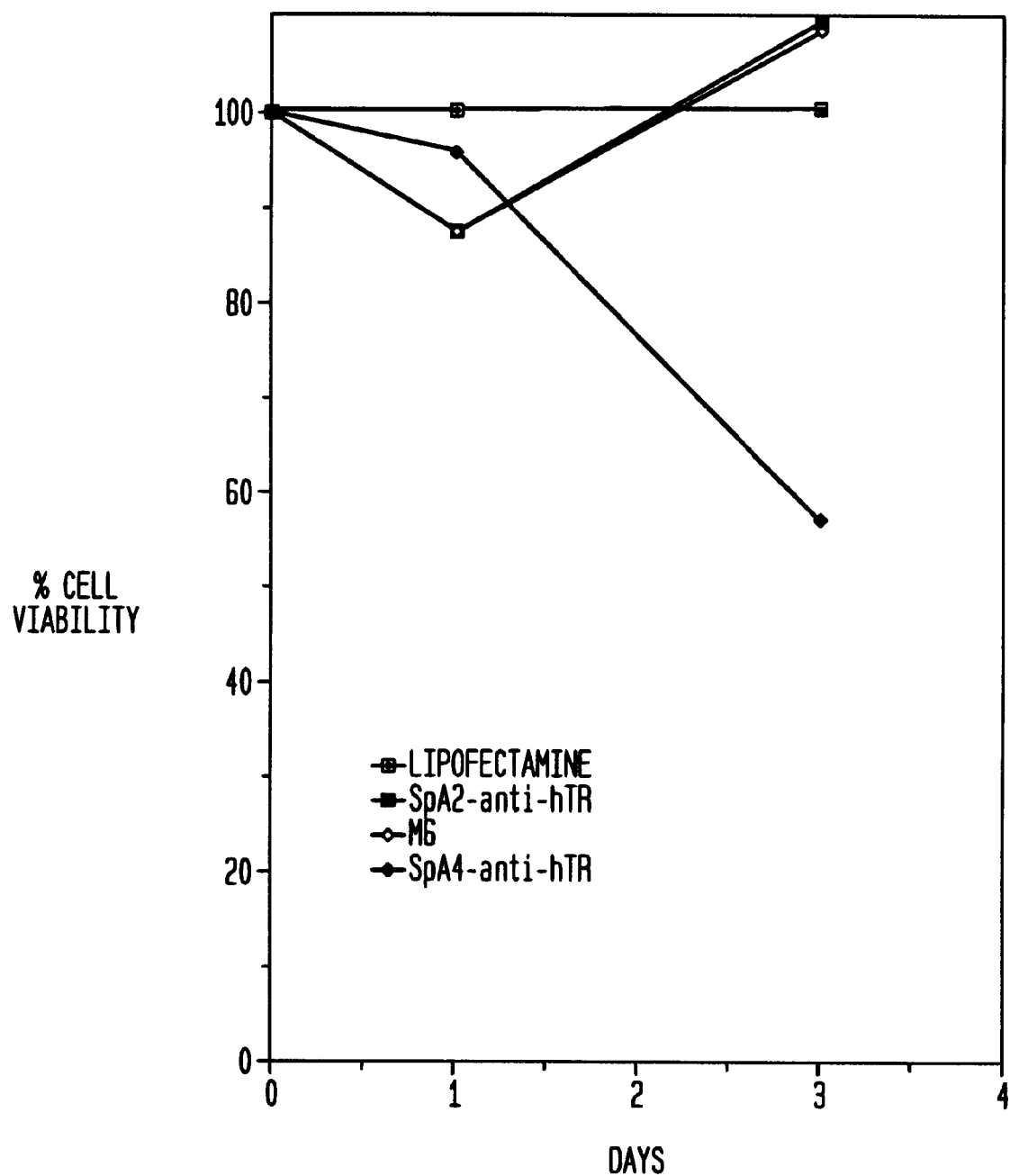

FIG. 7. $SpA_4$-anti-hTR specifically suppressed growth of RCC Renal Cell Carcinoma cells. Cells were treated daily with 0.5 micromolar $SpA_4$-anti-hTR, $SpA_4$-anti(M6)-hTR (labeled in the figure as M6), $SpA_2$-anti-hTR in the presence of lipofectamine, or with lipofectamine alone. Results are the average of duplicate assays.

Figure 8:
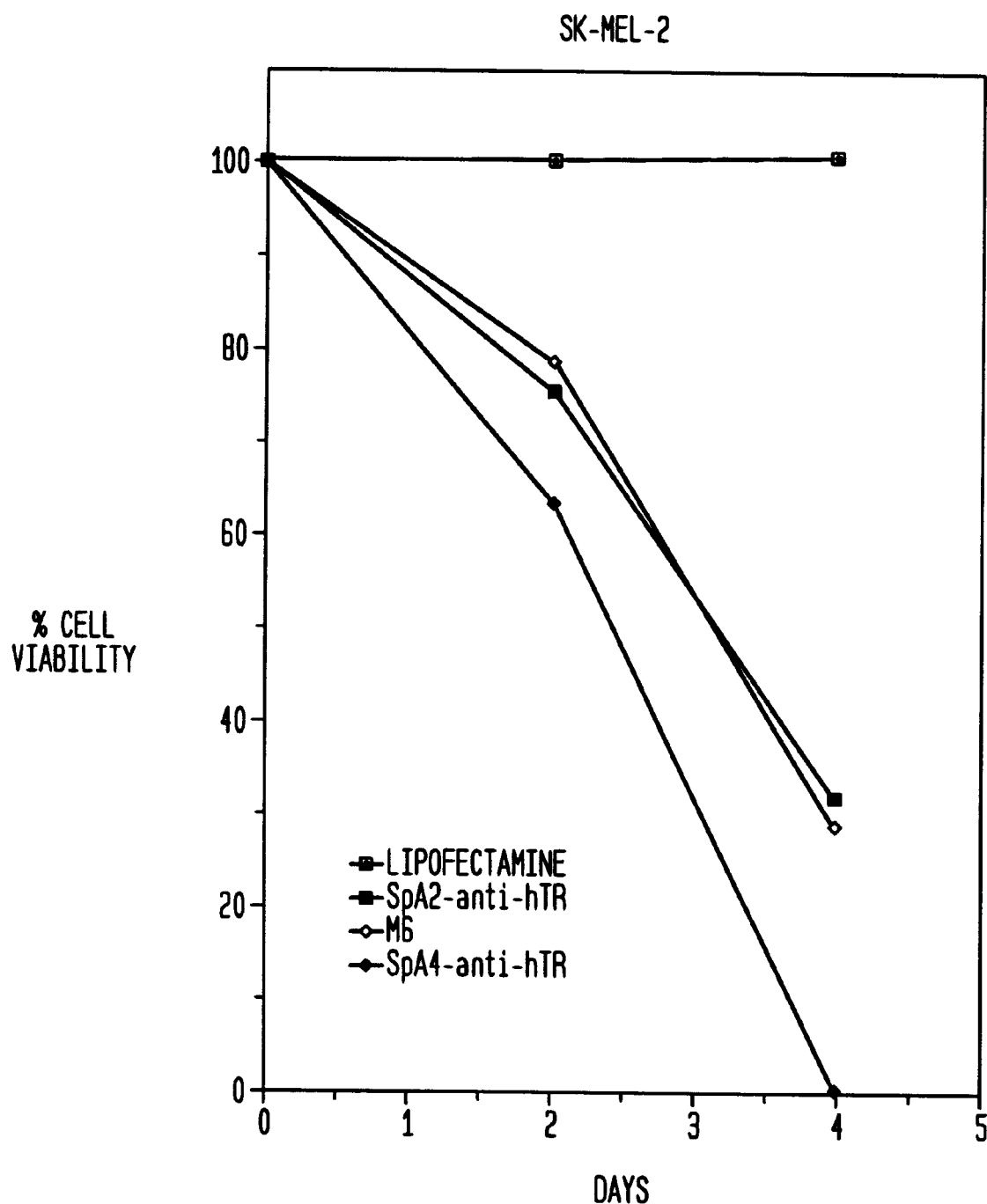

FIG. 8. $SpA_4$-anti-hTR specifically suppressed growth of SK-MEL-2 human melanoma cells. Cells were treated daily with 0.5 micromolar $SpA_4$-anti-hTR, $SpA_4$anti(M6)-hTR (labeled in the figure as M6), $SpA_2$-anti-hTR in the presence of lipofectamine, or with lipofectamine alone. Results are the average of duplicate assays.

Figure 9:
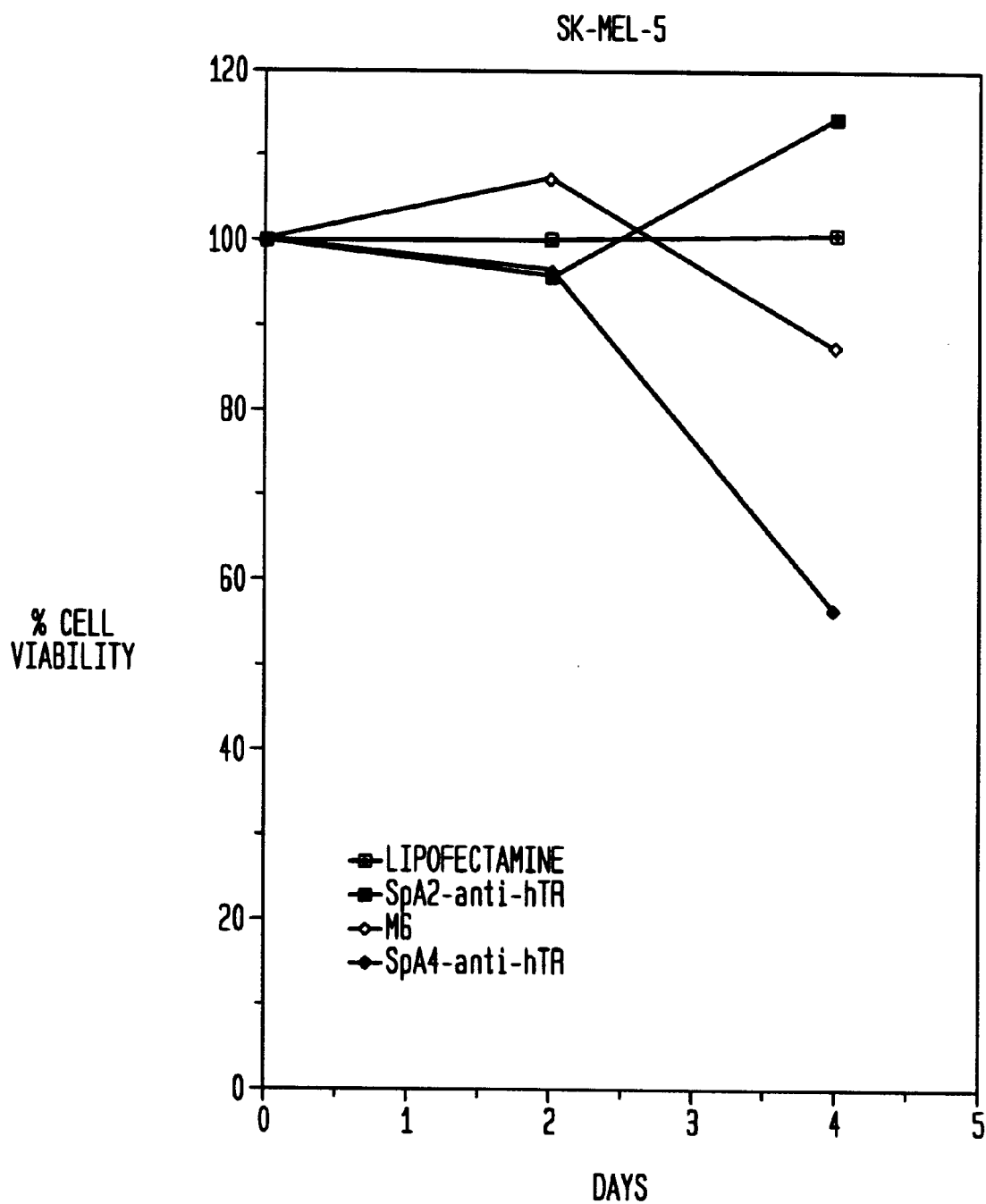

FIG. 9. $SpA_4$-anti-hTR specifically suppressed growth of SK-MEL-5 human melanoma cells. Cells were treated daily with 0.5 micromolar $SpA_4$-anti-hTR, $SpA_4$-anti(M6)-hTR (labeled in the figure as M6), $SpA_2$-anti-hTR in the presence of lipofectamine, or with lipofectamine alone. Results are the average of duplicate assays.

Figure 10:
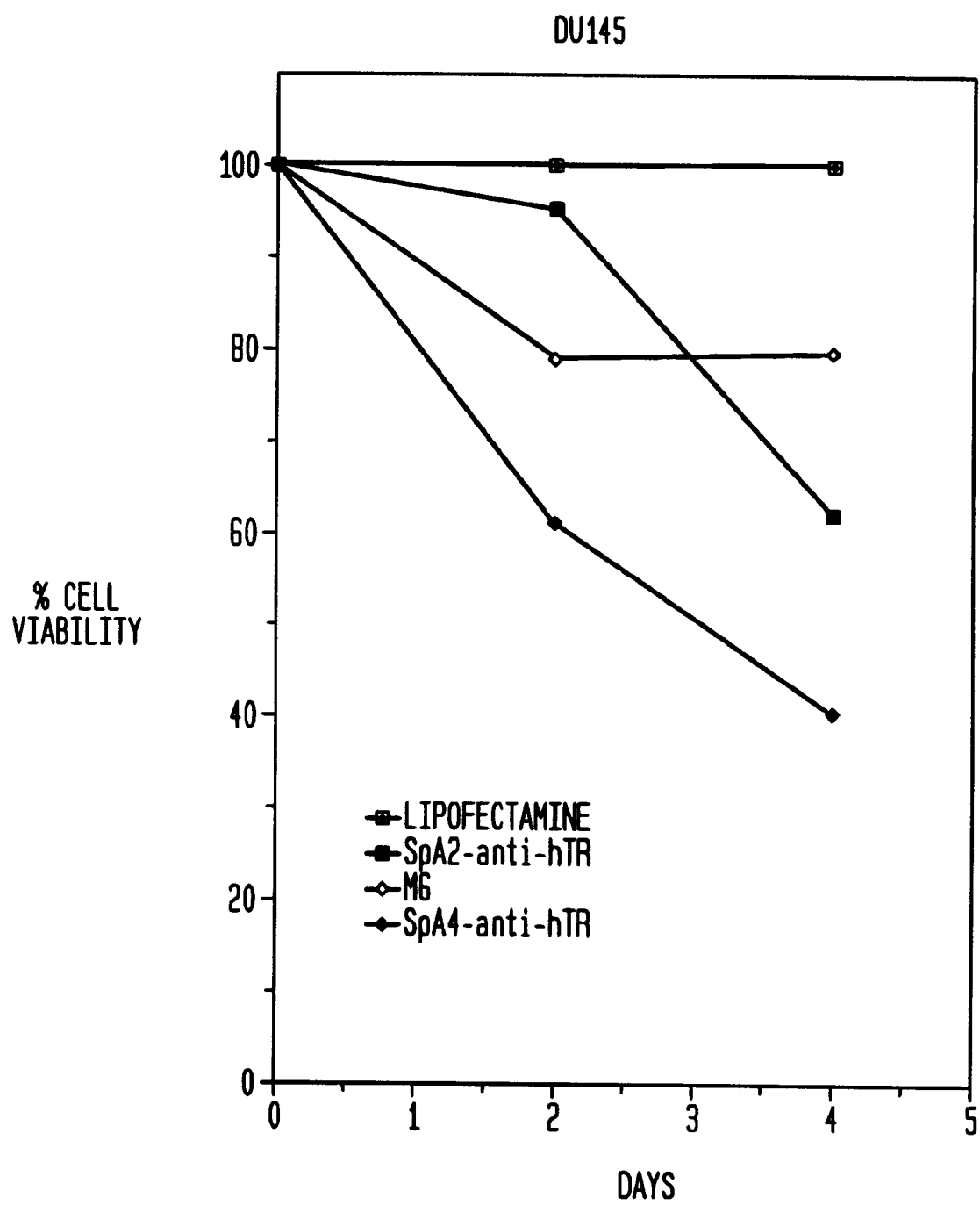

FIG. 10. $SpA_4$-anti-hTR specifically suppressed growth of DU145 human prostate cells. Cells were treated daily with 0.5 micromolar $SpA_4$-anti-hTR, $SpA_4$-anti(M6)-hTR (labeled in the figure as M6), $SpA_2$-anti-hTR in the presence of lipofectamine, or with lipofectamine alone. Results are the average of duplicate assays.

Figure 11:
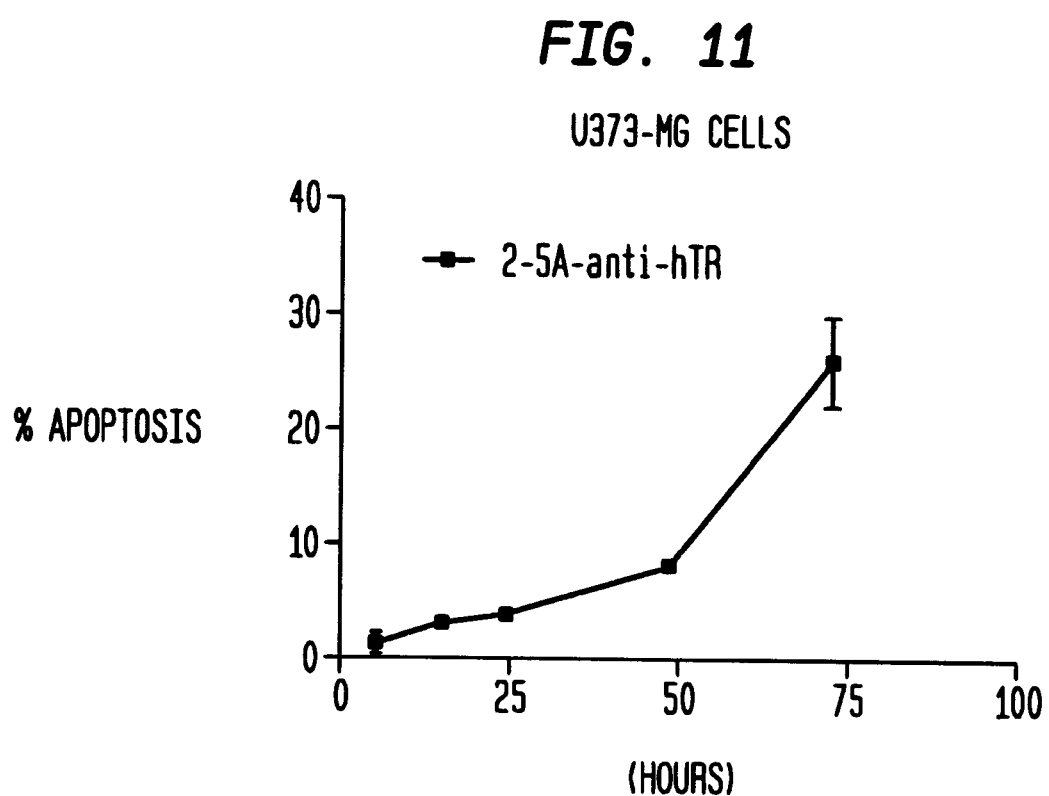

FIG. 11. SpA$_4$-anti-hTR treatment caused apoptosis of U373 human malignant glioma cells as determined by TUNEL assays.

Figure 12:
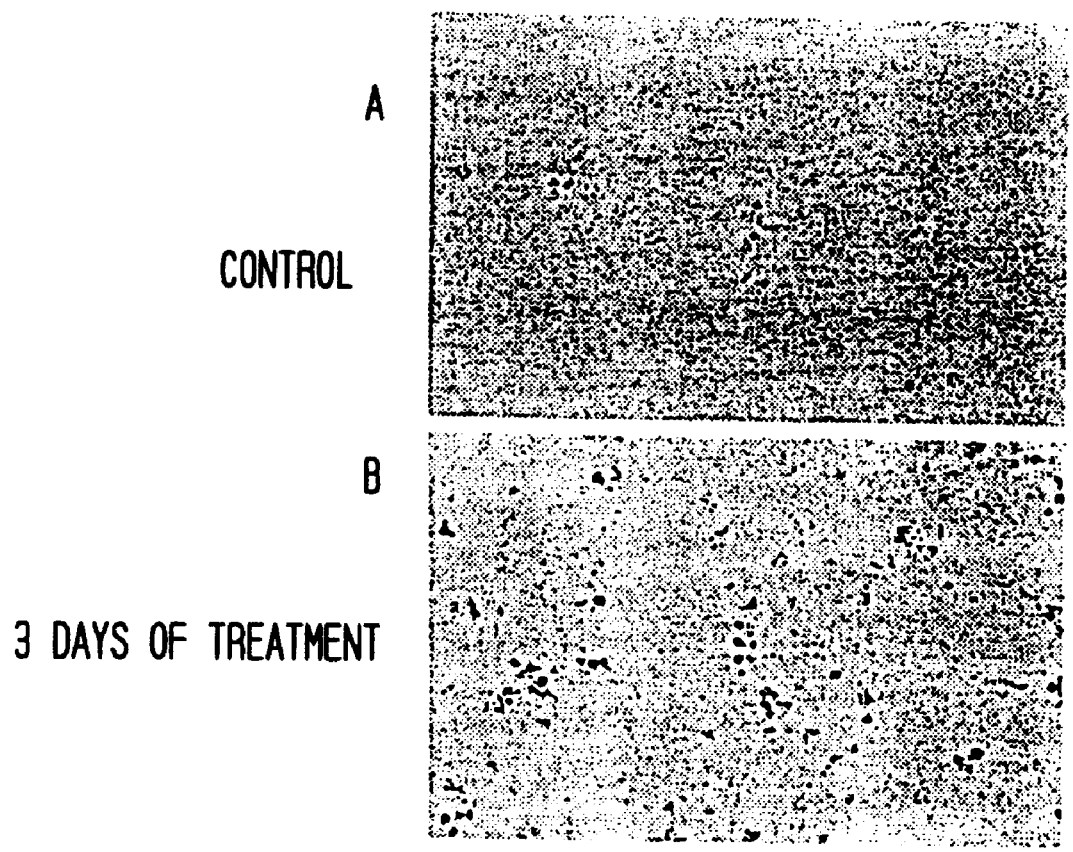

FIG. 12. TUNEL assays for apoptosis on FIG. 12A Control U373 cells, treated with lipofectamine once daily for three days and FIG. 12B U373 cells treated daily with 0.5 micromolar SpA$_4$-anti-hTR plus lipofectamine for 3 days.

Figure 13A:
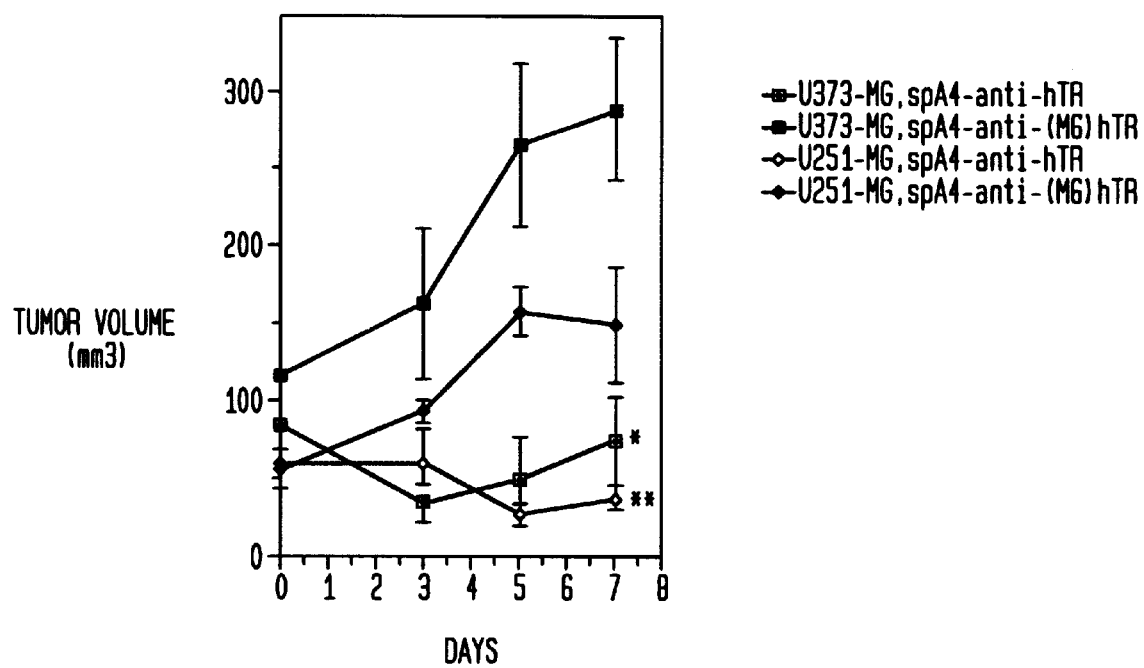
Figure 13B:
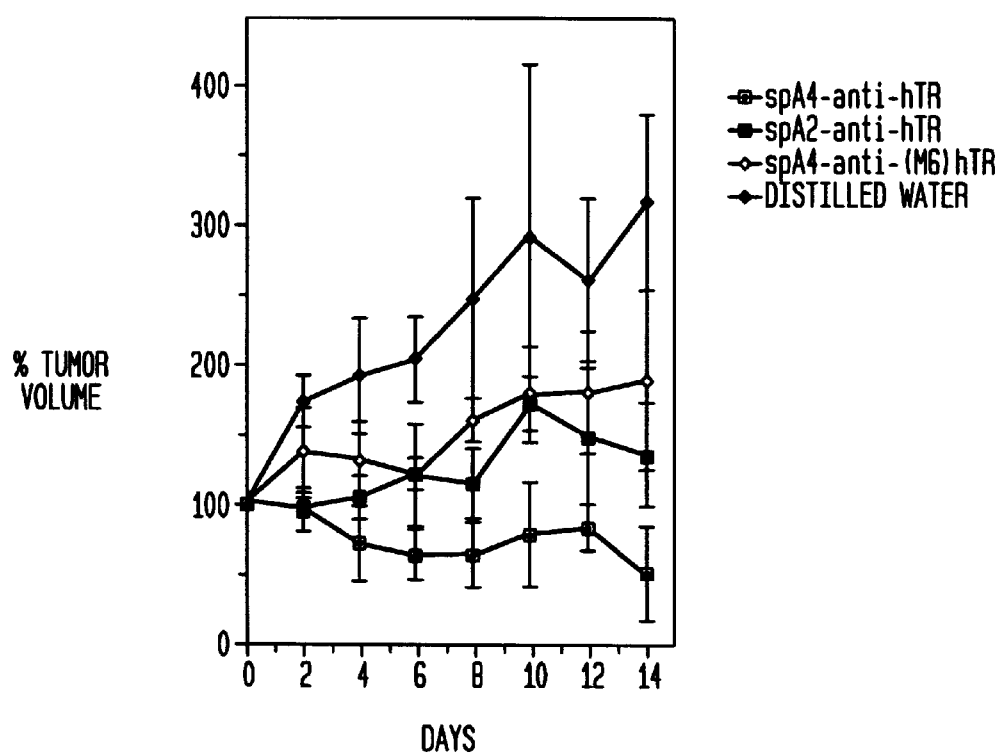

FIG. 13. Effect of 2-5A antisense telomerase on subcutaneous xenografts in nude mice. FIG. 13A Tumors from U251-MG and U373-MG cells were established subcutaneously in nude mice. After four or five weeks when the tumors were approximately 100 mm$^3$, oligonucleotides (5 nmol/20 microliters sterile distilled water) were administered directly into the tumors daily for 7 days. 5 mice were used in each treatment group. Tumor volume was then determined using calipers and the mean sizes S.D. were calculated. Tumors treated with spA$_4$-anti-hTR failed to grow progressively after commencement of the treatment. Those tumors treated with the spA$_4$-anti-(M6)hTR control oligonucleotide continued to increase in size throughout the treatment period. *P<0.01, and **P<0.03. FIG. 13B. When U251-MG tumors were treated for 14 days with spA$_4$-anti-hTR, the final tumor volume was reduced by 50% compared with the control treated tumors which show increases of 50–80%. By comparison with tumor growth rate seen in tumors treated with distilled water a mild antisense effect can be seen for the control oligos. In these plots tumor volume was expressed as a percentage of the original starting size before treatment.

Figure 14:

FIG. 14. In situ end-labeling of DNA in subcutaneous xenografts of nude mice. After treatment with oligonucleotides (5 nmol, every day) for 7 days, the mice were sacrificed and the subcutaneous mass was removed, frozen, and sectioned on a cryostat. The tumor specimens from U251-MG cells were counterstained by hematoxylin and eosin following the TUNEL technique. Arrows show representatives of tumor cells positive for DNA fragmentation (×400). (above) spA$_4$-anti-(M6)hTR, 7 Day; (below) spA$_4$-anti-hTR, 7 Day.

FIG. 15. Bar graph demonstrating the antiproliferative effect of SpA$_4$-anti-htR on renal cell carcinomas and human melanoma cells. Suppression of RCC, renal cell carcinoma, and A375 human melanoma cell growth by spA$_4$-anti-hTR. Cells were injected subcutaneously into nude mice. The treatment was started 8 days after implantations with oligonucleotide plus lipofectamine.

Figure 16A:
Figure 16B:
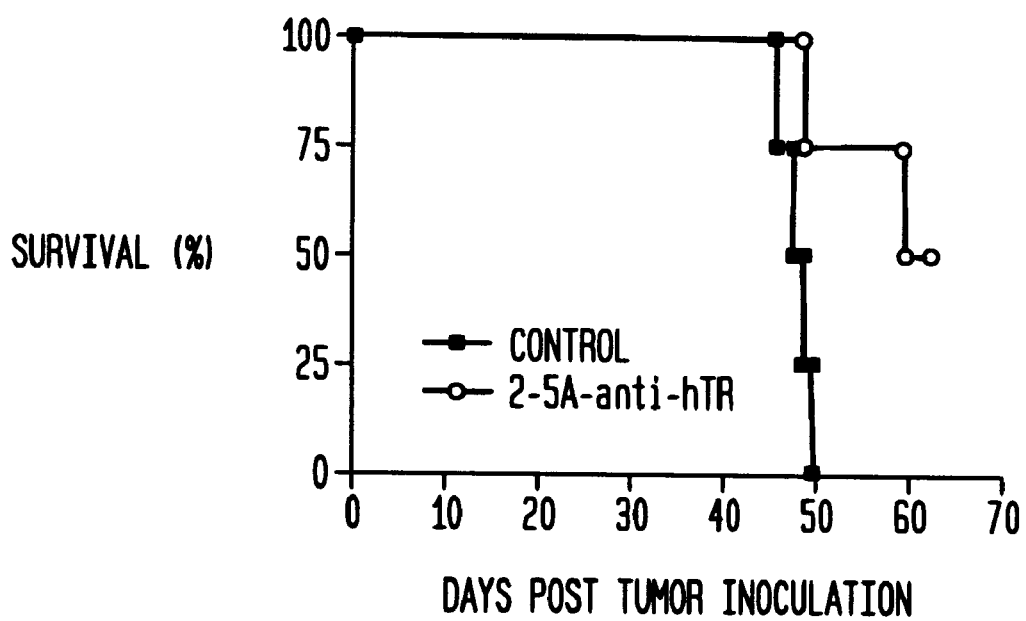

FIG. 16. Intracranial growth and treatments of human malignant glioma implants in nude mice. FIG. 16A Tumors infiltrating into surrounding normal tissues were clearly detected in untreated mice after two weeks. FIG. 16B Enhanced survival of mice injected with spA$_4$-antihTR.

Figure 17A:
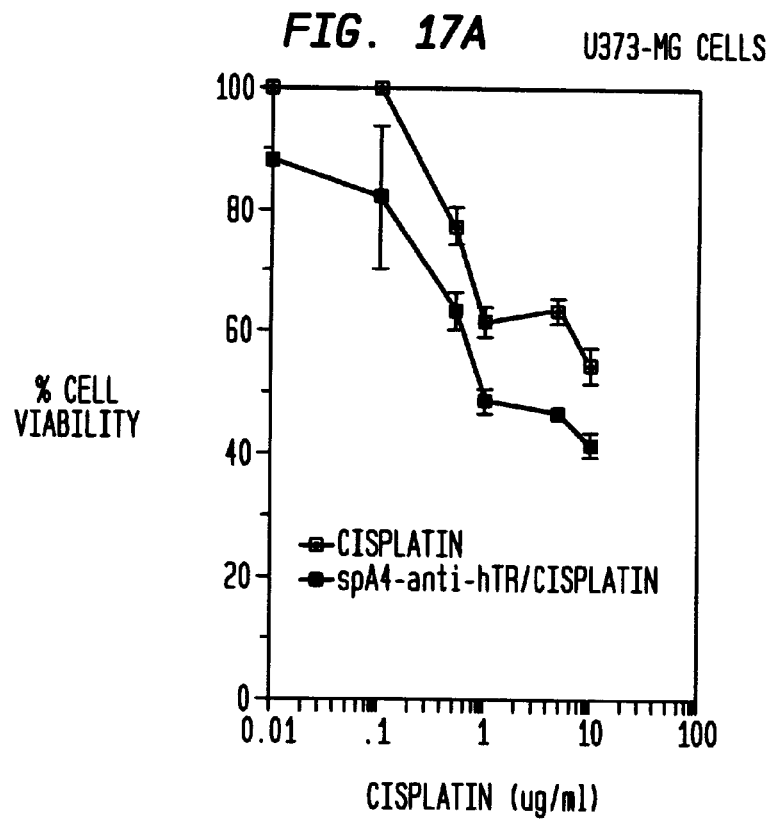
Figure 17B:
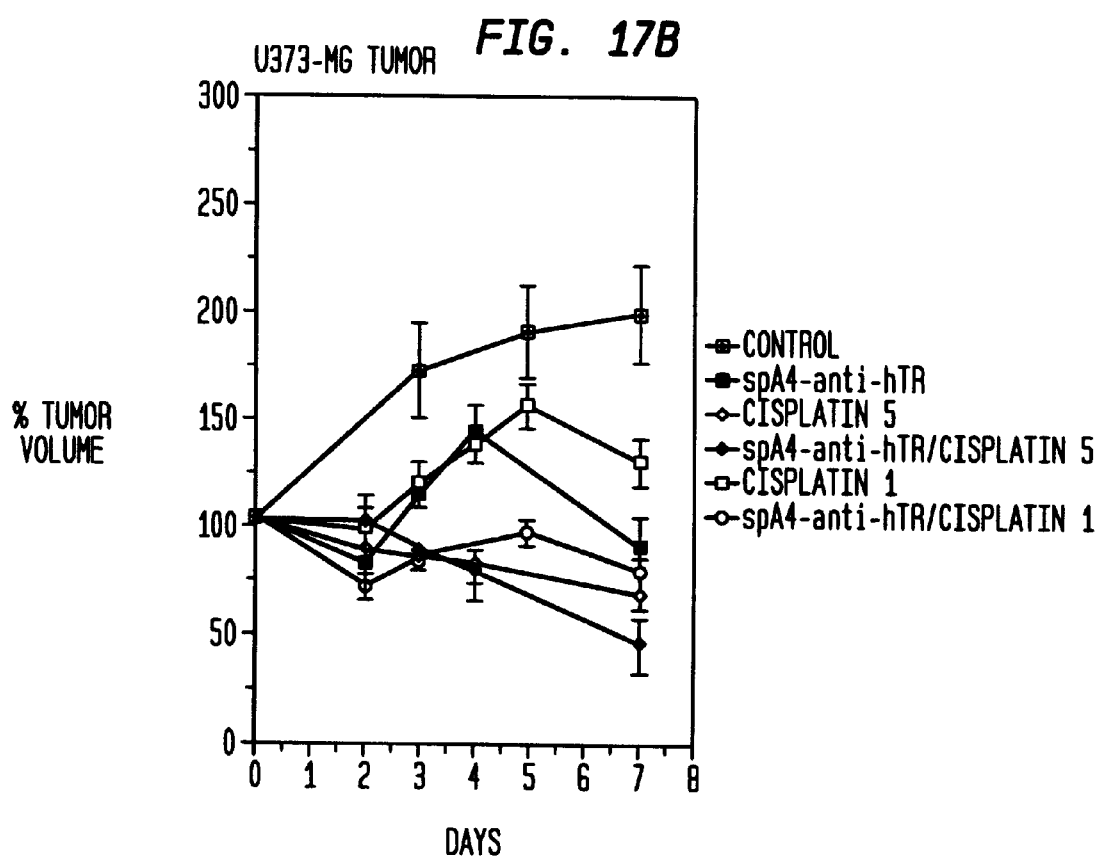

FIG. 17. Effect of combining 2-5A-anti-hTR with cisplatin on malignant glioma U373-MG cells in vitro and in vivo. FIG. 17A Tumor cells were treated with 2-5A-anti-hTR (0.5 µM, every 24 hr) mixed with Lipofectamine (1.0 µl/25 µl DMEM) or cisplatin for three days, and their viability was determined by MTT assay. Values represent the means±S.D. FIG. 17B Tumors from U373-MG cells (1.0× 10$^6$ cells in 0.05 ml serum free DMEM and 0.05 ml matrigel) were established subcutaneously in nude mice. After four or five weeks when the tumors were approximately 60–100 mm$^3$, spA$_4$-anti-hTR (5 nmol/20 µl sterile distilled water) were administrated directly into the tumors daily for 7 days. Cisplatin (1.0 or 5.0 mg/kg/mice) was administered intraperitoneally on Days 1, 3 and 5. Five Mice were used in each treatment group. Tumor volume was then determined using calipers, and the mean sizes ±S.D. were calculated.

Figure 18:
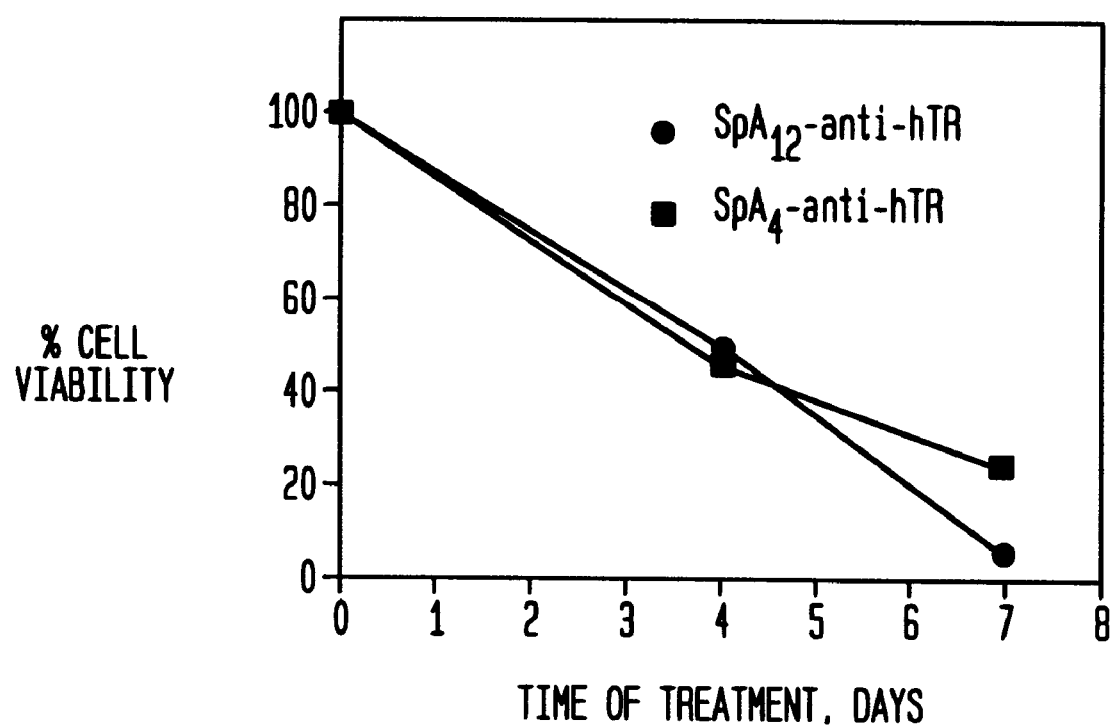

FIG. 18. Enhanced Anti-Tumor Cell Activity of SpA$_{12}$-anti-hTR. To determine the effect of extending the 2-5A moiety of 2-5A-anti-hTR, we have synthesized the following compound containing twelve 2',5'-linked adenylyl residues:

spA$_{12}$-anti-hTR Sp5'A(2'p5'A)$_{11}$-Bu$_2$-5'GCG CGG GGA GCA AAA GCA C3'-3'T5' (SEQ ID NO:2)

spA$_{12}$-anti-hTR or spA$_{12}$-anti-hTR, each at 0.5 micromolar, were mixed with lipofectamine and added daily to the U373 Cells.

5. DETAILED DESCRIPTION OF THE INVENTION

The present invention relates to methods of inhibiting telomerase activity with complexes of an activator of a ubiquitously expressed RNase, e.g. RNase L, and an oligonucleotide that is complementary to the ribonucleotide component of telomerase. The activator antisense complexes of the present invention specifically target and degrade the RNA component of telomerase. The complexes of the present invention act directly on the RNA component of telomerase to directly inhibit the enzymatic activity of the telomerase, as opposed to antisense oligonucleotides which act to inhibit telomerase gene expression and do not effect the activity of existing telomerase.

The present invention relates to an activator of RNase L and an oligonucleotide that is capable of binding to the RNA component of telomerase. In accordance with the present invention, the methods and complexes of the invention may be applied to target telomerase activity in a wide variety of cancer and tumor cells, in particular malignant brain tumors, prostate cancers, breast cancers, renal cancers and melanomas. In accordance with the present invention, the complex consists of an oligonucleotide that is capable of binding to the RNA component of a telomerase enzyme coupled to an RNase activator, so that the RNA component is cleaved and the telomerase enzyme activity is inhibited. In accordance with the present invention, the complex of the antisense oligonucleotide and the activator of RNase L may be covalently or non-covalently linked.

In a preferred embodiment of the present invention, the oligonucleotide component of the complex is complementary to a region of the RNA component of telomerase that is characterized by repeated or consensus sequences and/or is normally single stranded. The antisense oligonucleotide is between 12 and 25 nucleotides, preferably about 15 and about 20 nucleotides, and more preferably 19 nucleotides in length.

In a preferred embodiment the antisense oligonucleotide is complementary to a portion of the telomerase RNA that is normally single stranded. The activator is attached through a linker to either the 3' or the 5' terminus of the antisense oligonucleotide. In one embodiment, a blocker is attached to the 3' terminus of antisense oligonucleotide and the linker is attached to the 5' terminus of the antisense oligonucleotide. In an alternative embodiment the linker is attached to the 3' end of the antisense oligonucleotide and serves as both linker and blocker. The antisense oligonucleotide is between about 15 and about 20 nucleotides in length and preferably 17, 18 or 19 nucleotides in length. Those skilled in the art will understand that oligonucleotides with high GC content can be shorter than those with low GC content.

The internucleotide phosphodiester bonds of the antisense oligonucleotide can be any bonds that are compatible with the formation of Watson-Crick base pairs with complementary RNA. These include as non-limiting examples phosphodiesters, phosphorothiodiesters, methylphosphonodiesters and methylphosphonothiodiesters, which provide for increased resistance to degradation after administration. The nucleotides of the antisense oligonucleotide can be 2'-deoxynucleotides or 2'O-methyl nucleotides.

As demonstrated by the Applicants, the exposure of a human malignant glioma cell to a 2-5A-activator linked to a 19-mer antisense oligonucleotide targeted to the RNA component of telomerase (2-5A anti-hTR) effectively suppressed the growth of human malignant glioma cells, both in vitro and in vitro. The Applicants have further demonstrated that the 2-5A-anti-hTR are effective in inhibiting the growth of a broad range of cancer and tumor cells, including brain tumor cells, breast tumor cells, renal tumor cells and melanomas.

The present invention relates to pharmaceutical compositions comprising the 2-5A-activator-antisense oligonucleotides targeted to telomerase for the treatment and prevention of cell prolierative disorders, such as cancers and tumors, related to enhanced or elevated telomerase activity. The present invention relates to methods of treating and preventing cell proliferative disorders related to enhanced telomerase activity, including, but not limited to, brain cancer, breast cancer, prostate cancer, renal cancer and melanomas. The present invention further relates to combinatorial therapies in which the 2-5A-activator-antisense oligonucleotides targeted to the RNA component of telomerase are used in combination with other therapeutic agents, such as chemotherapeutic agents, to treat cell proliferative disorders. The combination of the 2-5A-activator-antisense oligonucleotide with a therapeutic agent to treat cancer may provide a means of chemosensitisation for malignant cells which are resistant to anticancer drugs.

5.1 ANTISENSE OLIGONUCLEOTIDES TARGETING THE RNA COMPONENT OF TELOMERASE

The invention in one embodiment consists of a complex of an activator of RNase L and an oligonucleotide that is complimentary to the RNA component of telomerase (human telomerase RNA, "hTR").

In accordance with the present invention, it is preferred to construct antisense oligonucleotides complementary to an "open" part of the telomerase RNA component, i.e., a region that is single stranded that normally has no self-hybridizing secondary structure, to ensure the maximum likelihood of achieving homologous binding. To determine the best target sequence, the telomerase RNA structure is analyzed using the MFOLD program (Salser, 1978, Cold Spring Harbor Symp. Quant. Biol. 42:985–1002; Zuker, 1989, Met. Enz. 180:262–288; Frier et al., 1986, Proc. Natl. Acad. Sci. USA 83:9373–9377). The predicted structure of telomerase RNA demonstrates that this molecule has very tight secondary folding which would make the binding of small oligonucleotides difficult (FIG. 1). The most "open" part of the molecule is seen between residues 76 and 94, 20 nucleotides 3' of the telomerase template sequence. Therefore in a preferred embodiment of the present invention, the 2-5A' antisense nucleotide targets the predicted loop comprising nucleotides 76 and 94. BLASTN searches of available databases for this nucleotide sequence reveal homologies only to human telomerase and a DNA sequence from *H. influenzae*. In another embodiment of the present invention, the 2-5A' antisense nucleotide targets any of the predicted open loops of the RNA component of telomerase, as shown in FIG. 1, in particular, the predicted open loop which comprises the telomerase template.

According to the invention, the portion of the hTR to which the antisense oligonucleotide is complementary can be determined from the sequence and secondary structure determining algorithms such as MFOLD. The result of this analysis, shown in FIG. 1, is that nearly all of the hTR is duplex. There was only one region having more than eight consecutive unpaired bases. That region is nucleotide 80 to 90. The sequence of hTR (nt 1 to 450) and downstream genomic sequence is given below:

```
GGGUUGCGGAGGGUGGGCCUGGGAGGGGUGGUGGCCAUUUUUUGUCUAACCCUAACUGAG  60   (SEQ ID NO: 1)
AAGGGCGUAGGCGCCGUGCUUUUGCUCCCCGCGCGCUGUUUUUCUCGCUGACUUUCAGCG  120
GGCGGAAAAGCCUCGGCCUGCCGCCUUCCACCGUUCAUUCUAGAGCAAACAAAAAAUGUC  180
AGCUGCUGGCCCGUUCGCCUCCCGGGGACCUGCGGCGGGUCGCCUGCCCAGCCCCCGAAC  240
CCCGCCUGGAGCCGCGGUCGGCCCGGGGCUUCUCCGGAGGCACCCACUGCCACCGCGAAG  300
AGUUGGGCUCUGUCAGCCGCGGGUCUCUCGGGGGCGAGGGCGAGGUUCACCGUUUCAGGC  360
CGCAGGAAGAGGAACGGAGCGAGUCCCGCCGCGGCGCGAUUCCCUGAGCUGUGGGACGUG  420
CACCCAGGACUCGGCUCACACAUGCAGUUCGCUUUCCUGUUGGUGGGGGGAACGCCGAUC  480
GUGCGCAUCCGUCACCCCUCGCCGGCAGUGGGGGCUUGUGAACCCCCAAACCUGACUGAC  540
UGGGCCAGUGUGCUGCAAAUUGGCAGGAGACGUGAAGGCACCUCCAAAGUCGGCCAAAAU  600
GAAUGGGCAGUGAGCCGGGGUUGCCUGGAGCCGUUCCUGCGUGGGUUCUCCCGUCUUCCG  660
CUUUUUGUUGCCUUUUAUGGUUGUAUUACAACUUAGUUCCUGCUCUGCAGAUUUUGUUGA  720
GGUUUUUGCUUCUCCCAAGGUAGAUCUCGACCAGUCCCUCAACGGGGUGUGGGGAGAACA  780
GUCAUUUUUUUUUGAGAGAUCAUUUAACAUUUAAUGAAUAUUUAAUUAGAAGAUCUAAAU  840
GAACAUUGGAAAUUGUGUUCCUUUAAUGGUCAUCGGUUUAUGCCAGAGGUUAGAAGUUUC  900
UUUUUUGAAAAAUUAGACCUUGGCGAUGACCUUGAGCAGUAGGAUAUAACCCCCACAAGC  960
UUU
```

In a preferred embodiment, the following sequence is used as the antisense component of the 2-5A activator-antisense complex:

5' GCG CGG GGA GCA AAA GCA C 3' (SEQ ID NO:1)

The present invention also encompasses variations of these sequences, including, but not limited to, one or more nucleotide substitutions, mismatches, truncations of these oligonucleotides, e.g. 12 to 18 residues of the above-identified oligonucleotides, and larger oligonucleotides which comprise the above-identified oligonucleotides, or 12 to 1819 residues thereof, or any other modification known to those skilled in the art, so that the antisense oligonucleotide still maintains the ability to specifically bind to the RNA component of telomerase.

The internucleotide phosphodiester bonds of the antisense oligonucleotide can be any bonds that are compatible with the formation of Watson-Crick base pairs with complementary RNA. These include as non-limiting examples phosphodiesters, phosphorothiodiesters, methylphosphonodiesters and methylphosphonothiodiesters, which provide for increased resistance to degradation after administration. The nucleotides of the antisense oligonucleotide can be 2'-deoxynucleotides, 2'fluoronucleotides or 2'O-alkyl, preferably 2'O-methyl nucleotides. The synthesis of 2'-O-alkyl-oligoribonucleotides, where the alkyl groups are methyl, butyl, allyl or 3,3-dimethylallyl is reviewed by Lamond, 1993, Biochem. Soc. Trans. 21, 1–8. Intermediates that are useful in the synthesis of 2'-O-methyl oligoribonucleotides are described in U.S. Pat. Nos. 5,013,830, 5,525,719 and 5,214,135, which are hereby incorporated by reference.

The synthesis of 2'-fluorophosphodiester and 2'-fluorophosphorothioate oligonucleotides can be performed according to teaching of Kawasaki, A. M., et al., 1993, J. Med. Chem. 36, 831-41 and WO 92/03568; the synthesis of P-alkyloxyphosphotriester-linked oligonucleotides and 2'-modified oligonucleotides can be performed according to U.S. Pat. No. 5,525,719, each of which is incorporated herein by reference. The synthesis of phosphorothioate oligodeoxynucleotides is taught by U.S. Pat. Nos. 5,276,019 and 5,264,423, which is hereby incorporated by reference. Synthesis of 2'-substituted oligonucleotides can be performed by variations on the techniques disclosed therein.

Peptide nucleic acids are also suitable for the practice of the invention. Peptide nucleic acids (PNA) are described in detail by Egholm et al., J. Am. Chem. Soc., 1992, 114, 1895 and Huang et al., J. Org. Chem., 1991, 56, 5006 and Patent Publication WO 92/20703 to Buchardt et al.; methods of making PBA/oligonucleotide chimeric polymers is described in WO 95/14706.

As used herein, the term "antisense oligonucleotide" denotes any polymer of pyrimidines and purines, and/or their analogs and derivatives that hybridizes in a sequence specific manner to RNA.

In a preferred embodiment the antisense oligonucleotide is complementary to a portion of hTR that is normally single stranded. The activator is attached through a linker to either the 3' or the 5' terminus of the antisense oligonucleotide by a linker. In one embodiment, a blocker is attached to the 3' terminus of antisense oligonucleotide and the linker is attached to the 5' terminus of the antisense oligonucleotide. In an alternative embodiment the linker is attached to the 3' end of the antisense oligonucleotide and serves as both linker and blocker. The antisense oligonucleotide is between about 12 and 25, preferably 15 and about 20 nucleotides and more preferably 18 or 19 nucleotides in length. Those skilled in the art will understand that oligonucleotides with high GC content can be shorter than those with low GC content.

5.2 THE STRUCTURE OF THE ACTIVATOR

In accordance with the present invention, chains of three or more 2', 5'-linked adenylyl residues are absolutely required for RNase L activation. Examples of the structure of the activator are described in patent publication WO94/09129, at pages 10, 45 and 46–51, which is hereby incorporated by reference. Briefly, the activator can contain at least three riboadenylate residues, linked by 2'-5'phosphodiester bonds, having a free 5' mono-, di- or triphosphate or thiophosphate. The 5' thiophosphate-tetraadenylate activator (sp5'A2'(p5'A2')$_3$-O-) is the preferred activator. Other activators include p5'A2'(p5'A2')$_2$-O-, sp5'A2'(p5'A2')$_2$-O-, and p5'A2'(p5'A2')$_3$-O-.

Phosphorothioate and phosphorodithioate linkages between adenine nucleosides can be used as well as phosphodiester. The use of these linkages results in decreased degradation but also decreased activity. (Beigelmann et al., 1995, Nucleic Acid Research 23:3989–94.) The use of a 5'-thiophosphate results in greatly improved activity and stability. Those skilled in the art appreciate that other nucleotides can be attached to the 3'hydroxyl or 2'hydroxyl of the 2'-5'tri- or tetra-adenylate without changing its activity as an RNase L activator. Thus, these embodiments are also included in the scope of the term "activator of RNase L." Those skilled in the art will further recognize that oligonucleotides containing bases other than adenine, such as inosine at the second nucleotide (counting 5'→13') can also be used. Those skilled in the art also recognize that non-nucleotide activators of RNase L can be used in the invention and are equivalents of nucleotide activators. As used herein the term "2-5A" refers to any nucleotide activator of RNase L and the term "activator of RNase L" refers to any activator of RNase L including 2-5A. The term 2',5'A refers specifically to 2',5'-linked oligoadenylates.

5.3 THE STRUCTURE OF THE ANTISENSE OLIGONUCLEOTIDES

The antisense oligonucleotide can have any structure now known or to be developed in the antisense art. These include phosphodiesters, phosphorothiodiesters, methylphosphonodiesters and methylphosphonothiodiesters, which provide for increased resistance to degradation after administration. The nucleotides of the antisense oligonucleotide can be 2'-deoxynucleotides or 2'O-methyl nucleotides.

The preparation of modified and unmodified oligonucleotides is well known in the art (reviewed in Agrawal et al., 1992, Trends Biotechnol. 10, 152–158; Agrawal in Protocols for Oligonucleotides and Analogs, Synthesis and Properties (Agrawal, ed.), Humana Press, Totowa, N.J. 1993, Chapter 20). For example, nucleotides can be covalently linked using art-recognized techniques such as phosphoramidate, H-phosphonate chemistry, or methylphosphoramidate chemistry (see, e.g., Uhlmann et al., 1990, Chem. Rev. 90, 543–584; Agrawal et al., 1987, Tetrahedron. Lett. 28, 3539–3542; Caruthers et al., 1987, Meth. Enzymol. 154, 287–313; U.S. Pat. No. 5,149,798). Oligomeric phosphorothioate analogs can be prepared using methods well known in the field such as methoxyphosphoramidite (see, e.g., Agrawal et al., 1988, Proc. Natl. Acad. Sci. USA 85, 7079–7083) or H-phosphonate (see, e.g., Froehler, 1986, Tetrahedron Lett. 27, 5575–5578) chemistry. The synthetic methods described in Bergot et al., 1992, J. Chromatog. 559, 35–42 can also be used.

5.4 THE STRUCTURE OF THE LINKER

Any linker that covalently connects an activator of RNase L and the antisense oligonucleotide and does not prevent the activator from activating RNase L can used. In a preferred embodiment the linker is attached to the 3' or 2' terminus of a 2-5A activator. In a further preferred embodiment the linker consists of a bis-1,4-butanediolphosphodiester which connects the 3' or 2' terminus of a 2-5A activator and the 5' or the 3' terminus of the antisense oligonucleotide. Attachment to a terminus of the antisense oligonucleotide is selected for the convenience of synthesis. Those skilled in the art appreciate that attachment to an internal 2' hydroxyl or to a portion of the nucleotide base that is not critical to base pairing are alternative embodiments of the invention.

5.5 PREFERRED EMBODIMENTS OF THE 2-5A ACTIVATOR ANTISENSE COMPLEXES

In a preferred embodiment of the present invention, the 2-5A activator-antisense complexes designed to target the RNA component of telomerase comprise an oligonucleotide component having the sequence:

5' GCG CGG GGA GCA AAA GCA C3' (SEQ ID NO:2)

The antisense oligonucleotide component may also comprise a 10 to 18 nucleotide fragment of the above-identified sequence or may also comprise a 20 to 25 nucleotide fragment which encompass all of a substantial portion of the above-identified oligonucleotide. In another embodiment, the present invention encompasses an antisense oligonucleotide component which is complementary to a region of the RNA component of telomerase. In a preferred embodiment the antisense oligonucleotide is complementary to one of the predited open loop structures of the RNA component of telomerase (see FIG. 1).

In another preferred embodiment of the present invention, the 2-5A activator-antisense complexes include, but are not limited to:

period of time and repeating this sequential administration, i.e., the cycle, in order to reduce the development of resistance to the therapies. The combination of the 2-5A activator antisense complexes of the present invention with chemotherapeutics have the added benefit of providing a means of chemosensitisation for cancer and tumor cells that are resistant to anticancer drugs. Examples of other chemotherapeutics which may be used in combination with the 2-5A activator antisense complexes of the present invention include, but are not limited to, cisplatin, doxorubicin, mitomycin, daunorubicin, bleomycin, actinomycin D, and neocarzinostatin.

Pharmaceutical compositions suitable for the practice of the invention include solutions of the activator antisense complex in carriers suitable for parenteral administration, such as physiologic saline, sterile water U.S.P., 5% glucose solution U.S.P. and the like. An increased efficiency of intracellular delivery of activator antisense complex can be obtained by complexing the oligonucleotides with polycationic soluble macromolecule or particulate carriers. Suitable particulate carriers include liposomes comprising polycationic lipids (see review Gao, X., & Huang, L., 1995, Gene Therapy 2, 710–722). Specific suitable lipids are described in U.S. Pat. Nos. 5,171,678 and 5,476,962 to Behr et al.; U.S. Pat. Nos. 5,264,618 and 5,459,127 to Felgner et al.; and in Bucherger et al., 1996, Biochemica 2, 7–10. A suitable soluble polycationic carrier that can be used to deliver the activator antisense complex is polyethylenimine, the use of which is described in Boussif et al., 1995, Proc Natl. Acad. Sci. USA 92, 7297–7301.

The dose of activator antisense complex that is effective can be determined using the animal model systems and

```
Sp5'A(2'p5'A)3-Bu2-5'GCG CGG GGA GCA AAA GCA C3'-3'T5';      (SEQ ID NO: 2)

Sp5'A(2'p5'A)12-Bu2-5'GCG CGG GGA GCA AAA GCA C3'-3'T5';     (SEQ ID NO: 2)

Sp5'A(2'p5'A)12-Bu2-5'GCG CGG GGA GCA AAA GCA C3'-3'T5;      (SEQ ID NO: 2)

Sp5'A(2'p5'A)-5'GsCsGs CGG GGA GCA AAAG CsAsCs 3'-3';        (SEQ ID NO: 8)

Sp5'A(2'p5'A)3-Bu2-5'-GsCsGs CGG GGA GCA AAAG CsAsCs 3'.    (SEQ ID NO: 8)
```

5.6 USE OF THE ACTIVATOR-ANTISENSE COMPLEXES

The activator antisense complexes of the present invention have a range of utility as therapeutics and diagnostics for proliferative cell disorders, including a broad range of cancers and tumors, related to enhanced or elevated telomerase expression and/or enzymatic activity. The activator antisense complexes of the invention can be administered by any technique that results in the introduction of the complexes into the nucleus of the malignant cells of the subject in need of treatment. In general any method of delivery that can be employed to administer conventional antisense oligonucleotides can be used to administer activator antisense complexes. Specific examples include direct injection into the primary site or a major metastatic site, intravenous administration, and intrathecal and intraperitoneal administrations for disease located in the arachnoid space or spinal canal and peritoneum, respectively.

In a further embodiment, the activator antisense complexes of the invention may be administered in combination with one or more other chemotherapeutic agents, such as cisplatin. The therapeutics may be administered simultaneously as an admixture or separately; or sequentially, including cycling therapies. Cycling therapy involves the administration of a first therapeutic for a period of time, followed by the administration of a second therapeutic for a pharmacokinetic techniques well known to those skilled in the art that have been developed to design treatments using conventional antisense oligonucleotides.

The activator antisense complexes of the invention can be used to treat any malignancy. In a preferred embodiment the activator antisense complexes are used by direct injection in a primary tumor that cannot be treated adequately by conventional surgery or irradiation alone because of its location next or within sensitive vital organs, for example glioblastoma multiform, which occurs in the brain and cannot be removed surgically.

Without limitation as to theory, it is believed that the inhibition of telomerase activity in malignant cells results in the death of the malignant cell by apoptosis. The activator antisense complexes work synergistically with other inducers of apoptosis. Thus, in a further embodiment of the invention the activator antisense complexes can be used in conjunction with conventional modes of oncological therapy, e.g, cytotoxic drugs and irradiation, which also cause apoptosis.

5.7 THERAPEUTIC USES

The invention provides for treatment or prevention of various cell proliferative diseases and disorders by administration of the 2-5A activator-antisense complex. Disorders involving tumorigenesis or cell overproliferation which result in enhanced telomerase activity are treated or prevented by administration of the 2-5A activator antisense complex that inhibits telomerase activity. See details in the subsections below.

Generally, it is preferred to administer a product of a species origin or species reactivity (in the case of antibodies) that is the same as that of the recipient. Thus, in a preferred embodiment, a 2-5A activator antisense complex comprises an antisense oligonucleotide complementary to human telomerase, is therapeutically or prophylactically administered to a human patient.

Additional descriptions and sources of 2-5A activator antisense complexes that can be used according to the invention are found in Sections 5.1 through 5.5 supra herein.

5.7.1 TREATMENT AND PREVENTION OF DISORDERS INVOLVING OVERPROLIFERATION OF CELLS

Diseases and disorders involving cell overproliferation are treated or prevented by administration of a 2-5A activator-antisense that inhibits telomerase activity.

In specific embodiments, 2-5A activator-antisense complexes that inhibit telomerase function are administered therapeutically (including prophylactically): (1) in diseases or disorders involving an increased (relative to normal or desired) level of telomerase protein or function, for example, in patients where telomerase protein is overexpressed, genetically defective, or biologically hyperactive; or (2) in diseases or disorders wherein in vitro (or in vivo) assays (see infra) indicate the utility of telomerase antagonist administration. The increased level in telomerase protein or function can be readily detected. A patient tissue sample may be obtained and a telomerase expression profile determined using a standard telomerase activity assay, i.e., TRAP assay. Many standard methods in the art can be thus employed to measure telomerase gene expression and/or activity. Cells extracts which produce a ladder of extended oligonucleotides with increasing sizes indicate the presence of telomerase activity. For example, malignant gliomas have been found to have high telomerase activity.

Diseases and disorders involving cell overproliferation which relate to enhanced or elevated levels of telomerase activity that can be treated or prevented include but are not limited to malignancies, premalignant conditions (e.g., hyperplasia, metaplasia, dysplasia), benign tumors, hyperproliferative disorders, benign dysproliferative disorders, etc. Examples of these are detailed below.

5.7.1.1 MALIGNANCIES

The 2-5A activator-antisense complexes of the present invention may be used to treat brain cancers, prostate cancers, breast cancers, renal cancers and melanomas. Malignancies and related disorders which are shown to be related to elevated or enhanced telomerase activity that can be treated or prevented by administration of a 2-5A' activator-antisense complex that inhibits telomerase activity include but are not limited to those listed in Table 1 (for a review of such disorders, see Fishman et al., 1985, *Medicine*, 2d Ed., J. B. Lippincott Co., Philadelphia):

TABLE 1

MALIGNANCIES AND RELATED DISORDERS

Leukemia
    acute leukemia
        acute lymphocytic leukemia
        acute lymphoblastic leukemia
        acute myelocytic leukemia
            myeloblastic
            myelogenous
            promyelocytic
            myelomonocytic
            monocytic
            erythroleukemia TABLE 1-continued

MALIGNANCIES AND RELATED DISORDERS chronic leukemia
        chronic myelocytic (granulocytic) leukemia
        chronic myelogenous leukemia
        chronic lymphocytic leukemia
Polycythemia vera
Lymphoma
    Hodgkin's disease
    non-Hodgkin's disease
Multiple myeloma
Waldenström's macroglobulinemia
Heavy chain disease
Solid tumors
    sarcomas and carcinomas
        adenocarcinoma
        fibrosarcoma
        myxosarcoma
        liposarcoma
        chondrosarcoma
        osteogenic sarcoma
        chordoma
        angiosarcoma
        endotheliosarcoma
        lymphangiosarcoma
        lymphangioendotheliosarcoma
        synovioma
        mesothelioma
        Ewing's tumor
        leiomyosarcoma
        rhabdomyosarcoma
        colon carcinoma
        colorectal adenocarcinoma
        colon tumor metastatic to brain
        lung carcinoma
        pancreatic cancer
        breast cancer
        ovarian cancer
        prostate cancer
        squamous cell carcinoma
        basal cell carcinoma
        adenocarcinoma
        sweat gland carcinoma
        sebaceous gland carcinoma
        papillary carcinoma
        papillary adenocarcinomas
        cystadenocarcinoma
        medullary carcinoma
        bronchogenic carcinoma
        renal cell carcinoma
        hepatoma
        bile duct carcinoma
        choriocarcinoma
        seminoma
        embryonal carcinoma
        Wilms' tumor
        cervical cancer
        uterine cancer
        testicular tumor
        lung carcinoma
        small cell lung carcinoma
        bladder carcinoma
        epithelial carcinoma
        glioblastoma
        glioma
        astrocytoma
        medulloblastoma
        craniopharyngioma
        ependymoma
        pinealoma
        hemangioblastoma
        acoustic neuroma
        oligodendroglioma
        meningioma
        melanoma
        neuroblastoma
        retinoblastoma In specific embodiments, malignancy or dysproliferative changes (such as metaplasias and dysplasias), or hyperproliferative disorders, are treated or prevented in the brain, breast, colon, prostate, lung, or skin. In other specific embodiments, carcinoma, melanoma, or leukemia is treated or prevented.

5.7.1.2 PREMALIGNANT CONDITIONS

The 2-5A activator-antisense complexes of the present invention that antagonize telomerase activity can also be administered to treat premalignant conditions shown to be related to enhanced or elevated telomerase activity and to prevent progression to a neoplastic or malignant state, including but not limited to those disorders listed in Table 1. Such prophylactic or therapeutic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a therapeutic that inhibits telomerase activity. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W. B. Saunders Co., Philadelphia, pp. 112–113) etc.)

In another specific embodiment, the 2-5A activator-antisense complexes of the invention is administered to a human patient to prevent progression to brain, breast, colon, prostate, lung, or skin. In other specific embodiments, carcinoma, melanoma, or leukemia is treated or prevented.

5.8 DEMONSTRATION OF THERAPEUTIC OR PROPHYLACTIC UTILITY

The 2-5A activator-antisense complex of the invention are preferably tested in vitro, and then in vivo for the desired therapeutic or prophylactic activity, prior to use in humans.

For example, In vitro assays which can be used to determine whether administration of a specific 2-5A activator-antisense complex is indicated, include in vitro cell culture assays in which a patient tissue sample is grown in culture, and exposed to or otherwise administered a 2-5A' activator-antisense complex, and the effect of the therapeutic upon the tissue sample is observed. In one embodiment, where the patient has a malignancy, a sample of cells from such malignancy is plated out or grown in culture, and the cells are then exposed to a 2-5A activator-antisense complex. The cells can first be assayed for decreased telomerase activity using telomerase assays described herein. A 2-5A activator-antisense complex which inhibits survival or growth of the malignant cells is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in orphology, etc.

In another embodiment, a 2-5A activator-antisense complex is indicated for use which exhibits the desired effect, inhibition of telomerase activity and inhibition of cell growth, upon a patient cell sample from tissue having or suspected of having a hyperproliferative disorder, respectively. Such hyperproliferative disorders include but are not limited to those described in Sections 5.7.1 through 5.7.2 infra.

In another specific embodiment, a 2-5A activator-antisense complex is indicated for use in treating cell injury or a degenerative disorder (see Section 5.9) which exhibits in vitro promotion of growth/proliferation of cells of the affected patient type.

In various specific embodiments, in vitro assays can be carried out with representative cells of cell types involved in a patient's disorder, to determine if a 2-5A activator-antisense complex has a desired effect upon such cell types.

In another embodiment, cells of a patient tissue sample suspected of being pre-neoplastic are similarly plated out or grown in vitro, and exposed to a 2-5A activator-antisense complex. The therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present. For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, *General Virology*, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the cell type upon which an effect is desired, according to the present invention.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.9 THERAPEUTIC/PROPHYLACTIC ADMINISTRATION AND COMPOSITIONS

The invention provides methods of treatment (and prophylaxis) by administration to a subject of an effective amount of the 2-5A activator-antisense complex of the invention. In a preferred aspect, the 2-5A activator-antisense complex is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

In a further embodiment, the activator antisense complexes of the invention may be administered in combination with one or more other chemotherapeutic agents, such as cisplatin. The therapeutics may be administered simultaneously as an admixture or separately; or sequentially, including cycling therapies. Cycling therapy involves the administration of a first therapeutic for a period of time, followed by the administration of a second therapeutic for a period of time and repeating this sequential administration, i.e., the cycle, in order to reduce the development of resistance to the therapies. The combination of the 2-5A activator antisense complexes of the present invention with chemotherapeutics have the added benefit of providing a means of chemosensitisation for cancer and tumor cells that are resistant to anticancer drugs. Examples of other chemotherapeutics which may be used in combination with the 2-5A activator antisense complexes of the present invention include, but are not limited to, doxorubicin, mitomycin, daunorubicin, bleomycin, actinomycin D, and neocarzinostatin.

Formulations and methods of administration that can be employed are described hereinbelow.

Various delivery systems are known and can be used to administer a Therapeutic of the invention, e.g., encapsulation in liposomes, microparticles, microcapsules, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the 2-5A activator-antisense complex can be delivered in a vesicle, in particular a liposome (see Langer, 1990, Science 249:1527–1533; Treat et al. 1989, in Liposomes in the Therapy of Infectious Disease and Cancer, Lopez-Berestein and Fidler (eds.), Liss, New York, pp. 353–365; Lopez-Berestein, ibid., pp. 317–327; see generally ibid.).

In yet another embodiment, the therapeutic can be delivered in a controlled release system. In one embodiment, a pump may be used (see Langer 1987, supra; Sefton, CRC Crit. Ref. Biomed. Eng. 14:201; Buchwald et al. 1980, Surgery 88:507; Saudek et al. 1989, N. Engl. J. Med. 321:574). In another embodiment, polymeric materials can be used (see Medical Applications of Controlled Release, Langer and Wise (eds.), CRC Pres., Boca Raton, Fla. 1974; Controlled Drug Bioavailability, Drug Product Design and Performance, Smolen and Ball (eds.), Wiley, New York 1984; Ranger et al. 1983, J. Macromol. Sci. Rev. Macromol. Chem. 23:61; see also Levy et al. 1985, Science 228:190; During et al. 1989, Ann. Neurol. 25:351; Howard et al. 1989, J. Neurosurg. 71:105). In yet another embodiment, a controlled release system can be placed in proximity of the therapeutic target, i.e., the brain, thus requiring only a fraction of the systemic dose (see, e.g., Goodson 1984, in Medical Applications of Controlled Release, supra, vol. 2, pp. 115–138).

The amount of the 2-5A activator antisense complexes of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20 μg to 100 mg micrograms of active compound per kilogram body weight. Suitable dosage ranges for intranasal administration are generally about 0.01 pg/kg body weight to 100 mg/kg body weight. Effective doses may be extrapolated from dose-response curves derived from in vitro or animal model test systems.

6. EXAMPLE: SYNTHESIS OF 2-5A' ACTIVATOR-ANTISENSE COMPLEXES

The following is an example of the modified automated or semi-automated procedures which may be used to synthesize the 2-5A activator antisense complexes of the present invention. However, any technique or method known to those skilled in the art to synthesize oligonucleotides may be used in substitution for the methods described herein.

6.1 MATERIALS AND METHODS

Hereinafter activator-antisense complexes wherein the activator is a 2',5'A are termed "2-5A antisense chimeras." Synthesis and Purification of 2-5A Antisense Chimeras Oligonucleotide Structural Types Synthesized The following generic oligonucleotide types were prepared for this study. Oligonucleotides $spA_4$-anti-hTR and $spA_2$-anti-hTR contain the sequence 5'GCG CGG GGA GCA AAA GCA C3' (SEQ ID NO: 2). Oligonucleotide $spA_4$-anti-(M6)hTR contains six mismatched bases sequence 5'GC<u>C</u> CG<u>C</u> GG<u>T</u> GC<u>T</u> AA<u>T</u> GC<u>T</u> C3' (SEQ ID NO: 3). The underlined nucleotides are not complementary to hTR.

The following procedures are illustrative of those employed to synthesize the activator-antisense complexes. In general, they follow the synthetic strategy developed in Lesiak et al., 1993, Bioconjugate Chem. 4,467–472; Xiao et al., 1994, Bioorganic & Med. Chem. 4, 2609; Was, W. et al., 1996, Antisense Nucleic Acid Drug Dev., 6, 247–258.

Reagents and Chemicals Employed

1. For Initiation of Synthesis on Solid Support
dT-5'-lcaa-CPG (500 Å)
3'-0-dimethoxytritylthymidine-5'-lcaa-CPG
This solid support was obtained from Glen Research (Sterling, Va.) and was used to synthesize oligonucleotides with and inverted 3'-3' terminal phosphodiester bond. It was 10 μmole size.

2. Elongation of the DNA Antisense Chain

For normal 3→5' phosphodiester bond oligonucleotides, a total of 500 mg of each of the following phosphoramidites (Applied Biosystems) was dissolved in the indicated amount of anhydrous acetonitrile to make a 0.1 M phosphoramidite solution:
5'-O-dimethoxytrityl-N6-benzoyl-2'-deoxyadenosine-31-(2-cyanoethyl-N,N-diisopropyl)phosphoramidite (5.6 mL)
5'-O-dimethoxytrityl-N4-benzoyl-2'-deoxycytidine-31(2-cyanoethyl-N,N-diisopropyl)phosphoramidite (5.9 mL)
5'-O-dimethoxytrityl-N2-isobutyryl-2'-deoxyguanosine-31-(2-cyanoethyl-N,N-diisopropyl)phosphoramidite (5.8 mL)
5'-O-dimethoxytrityl-2'-deoxythymidine-3'-(2-cyanoethyl-N,N-diiso propyl)phosphoramidite (6.6 mL)

3. Linker to Join Chimeric Domains

The linker, (2-cyanoethyl-N,N-diisopropyl)-[4-O-(4,4'-dimethoxytrityl) butyl]phosphoramidite, was obtained from Chemgene Corp. (Waltham, Mass., Cat. No. RN9775), and a 0.2 M solution was made by dissolving 250 mg linker in 2.1 mL of anhydrous acetonitrile.

4. For synthesis of 2',5'-Oligoadenylate Domain of the Chimera
5'-O-dimethoxytrityl-N6-benzoyl-3'-O-t-butyldimethylsilyladenosine-2'-N,N-di-isopropylcyanoethylphosphoramidite (ChemGenes Corp., Waltham, Mass., cat no. ANP 5681). A 0.1 M solution was made by dissolving 500 mg of monomer in 5.0 mL of anhydrous acetonitrile.

5. Phosphorylation Reagent for 5'-Terminus of 2',5'-Oligoadenylate Domain of Chimera
2-[2-(4,4'-dimethoxytrityl)ethylsulfonyl]ethyl-(2-cyanoethyl)-(N,N-diisopropyl)-phosphoramidite (Glen Research, Sterling, Va. cat no. 10-1900-90) was used at a concentration of 0.1 M in anhydrous tetrazole/acetonitrile (ABI) for the phosphorylation of 5'-terminus of 2',5'-oligoadenylate domain of chimera.

6. Other Reagents

All other DNA synthesis reagents were obtained from Applied Biosystems Inc. which includes diluent (acetonitrile), activator solution (tetrazole/acetonitrile), capping solutions (A: acetic anhydride solution and B: N-methylimidazole solution), deblocking reagent (trichloroacetic acid solution), oxidizer (iodine solution), and tetraethylthiuram disulfide sulfurization reagent.

Tetrabutylammonium fluoride in tetrahyrofuran (Aldrich, Milwaukee, Wis.) was used to deblock the t - butyldimethylsilyl group used for protection of the 3'-hydroxyls of (2',5')-oligoriboadenylate domain.

6.2 SYNTHESIS PROCEDURE

The 2',5'-oligoadenylate/antisense chimeras were synthesized by modified automated procedure.

All of the chemicals were dried over $P_2O_5$ in vauco overnight before use. The 10 μmole deoxynucleoside-lcaa-CPG column was used.

The (2',5')-oligoadenylate/antisense chimera refers to the complete 2',5'A-antisense chimera and has four regions defined for synthetic purposes: an antisense region, a linker region, (2',5')-oligoadenylate region and a thiophosphate region. The 2',5'A-antisense chimera was synthesized by the automated method listed below:

| Oligonucleotide: | Sequence: | |
|---|---|---|
| spA4-anti-hTR | Sp5'A2'p(5'A$_2$p)$_3$-[(Bu)p]$_2$-5'GCG CGG GGA GCA AAA GCA C3'-3'T5' | (SEQ ID NO: 2) |
| spA2-anti-hTR | Sp5'A2'p5'A$_2$p-[(Bu)p]2-5'GCG CGG GGA GCA AAA GCA C3'-3'T5' | (SEQ ID NO: 2) |
| spA4-anti-(M6)hTR | Sp5'A2'p(5'A$_2$p)$_3$-[(Bu)p]$_2$5' GC<u>C</u> CG<u>C</u> GG<u>T</u> GC<u>T</u> AA<u>T</u> GC<u>T</u> C3'-3'T5' | |

Bu - butanediol linkers.

| synthesis region (sequence edit) | coupling time (seconds) | coupling reagents & concentration | trityl mode |
|---|---|---|---|
| DNA antisense | 15 | 0.1M monomer in acetonitrile | trityl on |
| linker | 300 | 0.2M linker in acetonitrile | trityl on |
| (2',5')oligoadenylate | 600 | 0.1M (2',5')Ado$^{BZ}$ in acetonitrile | trityl on |
| thiophosphate* | 120 | 0.1M P$^{III}$ reagent in acetonitrile | trityl off |

*Sulfurization time is 2 × 900 seconds with TETD.

10 μmole scale standard synthesis cycle was used. The cycle was modified by changing the coupling time (coupling of monomer) for each different region. The monomer/acetonitrile solution was installed on the DNA synthesizer by a double change procedure to avoid contaminants. After the synthesis of each region, the column was dried completely by Argon for at least 3 min. and the synthesis cycle, trityl mode, and sequence were edited for the synthesis of next region of the desired oligonucleotide.

Cleavage and Deprotection

1. The oligonucleotide was cleaved from the CPG support by concentrated ammonium hydroxide/ethanol (3:1 v/v) at room temperature for 2 hours.

2. The ammonium hydroxide/ethanol solution of crude oligonucleotide was removed into a vial and sealed tightly. The solution was incubated at 55° C. for 8 hours to remove the protecting groups on the bases.

3. The resulting ammonium hydroxide/ethanol solution of oligonucleotide was transferred to a glass tube, and cooled completely in a ice-bath. The solution was then evaporated to dryness in a speedvac concentrator and a solution of tetrabutylammonium fluoride (3 mL, 1.0 M) in THF was added to each tube, and the entire mixture was vortexed for at least 1 min. This reaction mixture was allowed to incubate at room temperature for at least 10 hours.

A half volume of 0.1 M TEAA (tetraethylammonium acetate) (pH 7.0) buffer was added, mixed and evaporated to half volume to remove THF. The residue was subjected to purification by HPLC.

Purification of the Oligonucleotides

Polystyrene Reverse-Phase Ion-Pair Chromatography (PRP-IPC) Protocol (a modification of the method of Swiderski, et al., 1994, Analytic Biochem. 216, 83–88).

The oligonucleotide was diluted with water, filtered through 0.45 mm millipore membrane filter to make a clear solution, and the clear solution was directly injected into the preparative PRP-1 HPLC column 250×21.5 mm, Hamilton Co., Reno, Nev.

| Solvent A: | 10 mM tetrabutyl ammonium phosphate (TBAP), pH 7.5 in water. |
|---|---|
| Solvent B: | 10 mM TBAP, pH 7.5 in acetonitrile/water (8:2 v/v). |

The sample was eluted with a convex gradient of 5–90% solvent B in A in 60 min. at a flow rate of 5.0 mL/min.

Fractions containing desired oligo were pooled and evaporated to about 4–5 mL.

Fractions containing desired oligo were pooled and evaporated to about 4-5 mL. The salt from the column was removed by passing oligonucleotide solution through C-18 Sep-Pak cartridge. The oligo-TBA ion pair was then converted into its sodium salt form by following ethanol-NaCl precipitation procedure:

Evaporate the desalted oligo solution to dryness. Dissolve the resultant residue in 300 μL of 1.0 M NaCl by vortex. Precipitate the oligo by adding 1 mL of 200 proof ethanol drop-wise while vortexing. Chill on ice for at least 30 minutes. Centrifuge for about 5 minutes. Carefully remove supernatant. Repeat the precipitation procedure one more time.

Dialysis of (2',5')-Oligoadenylate/antisense Chimeras

After Purification by HPLC, C-18 cartridge and ethanol precipitation, the oligonucleotide (sodium salt) was dialyzed to remove small molecules and excess salt. The dialysis was carried out at 4° C. The oligonucleotide was dialyzed against water for 24 hours.

Post-treatment of Oligoadenylate/antisense Chimeras

The oligonucleotide, after dialysis, was passed through a 0.22 μ millex-GV filter unit (Millipore, Cat. No. SLGVO25LS) for sterilization. The resulting solution was quantitated as O.D. A260 by UV/Vis spectrophotometry.

Nucleotide composition analysis of (2',5')-Oligoadenylate/Antisense Chimeras

1. Nucleotide Composition Analysis

The nucleotide composition of the chimeric oligonucleotide were analyzed by enzymatic digestion with snake venom phosphodiesterase (Crotallus durissus) (Pharmacia, cat # 27,0821-01). Under the condition described by Xiao et al., 1994, Bioorganic & Med. Chem. 4, 467.

A purified oligonucleotide (0.2 A260 O.D.U.) is incubated with snake venom phosphodiesterase (0.15 units) in 50 mM Tris/HCl, pH 8.0, 0.5 mM MgCl$_2$, pH 8.0. The 100 μL mixture was incubated at 37° C. for at least 4 hours.

After digestion, the solution was treated with Microcon-10 (Amicon, Inc. product No. 42406). The microcon was first spin-rinsed with water before addition of 100 μL sample solution. The centrifuge time was typically 45 min. The clear solution was used for HPLC analysis.

An aliquot (5–10 μL) of the hydrolysate was analyzed by reverse phase HPLC using a Beckman Ultrasphere C-18 ODS column (0.46×25 cm). Separation of the digestion products was accomplished under the following conditions: 2% B isocratically for 20 min. linear gradient 2–50% B for 15 min. and held isocratically 10 min where solvent A was 100 mM ammonium phosphate, pH 5.5 and solvent B was methanol/water (1:1 v/v). The flow rate was 0.5 mL/min. The standard markers dCMP, TMP, dGMP, AMP and dAMP (Aldrich Chem. Co.) were used to compare retention times and elution orders of the hydrolysis products. Typically, the peaks obtained from the enzymatic hydrolysis of an oligonucleotide had retention times of 9.7 min. (dCMP), 27.3 min. (TMP), 29.6 min. (dGMP), 31.7 min. (AMP), 39.5 min. (Alinker) and 41.2 min. (dAMP). The retention times varied depending on the column, pH value of mobile phase and the equilibrium times of the column. The integrated peak areas provided the relative content of each nucleotide. The extinction coefficients of 7610 (dCMP), 8158 (TMP), 9969 (dGMP), 12342 (AMP & Alinker), 14361 (dAMP) measured at 260 nm in 100 mM ammonium phosphate, pH 5.5 were used in the analysis.

Oligonucleotide Purity Confirmation

The purities of (2',5')-oligoadenylate/antisense chimeras were checked by HPLC.

Dionex PA-100 Ion Exchange HPLC Method

The purities of oligonucleotides could also be measured by a Dionex Ion exchange HPLC. Usually, the dionex PA-100 ion exchange column could provided higher resolution and better peak shape compared with other HPLC chromatographic method for the analysis of (2',5')-oligoadenylate/antisense chimera.

A typical chromatogram of (2',5')-oligoadenylate/antisense was obtained by the following conditions: Dionex PA-100 (4×250 mm) column (Dionex, cat # 43010). Solvent A was 25 mM Tris/HCl and 0.5% acetonitrile (pH 7.0), solvent B was 25 mM Tris/HCl, 0.5% acetonitrile and 1 M ammonium chloride (pH 7.0). The sample was eluted in linear gradient of 10–70% B in A during 30 min. and held isocratically for 10 min. at a flow rate of 1 mL/min. Detection was at 260 nm.

7. EXAMPLE: RNase L ACTIVATORS WHICH INHIBIT TELOMERASE EXPRESSING MALIGNANCIES This study demonstrates that 2-5A-anti-hTR is a potent anticancer agent against human tumor cells implanted into nude mice. By treating malignant glioma cells in culture with 2-5A-antisense against telomerase RNA the vast majority of cells can be killed within 14 days. When the antisense molecules are injected directly into tumors induced subcutaneously in nude mice, the tumor mass is significantly reduced by 50% over a 14 day period. A broad-specificity anti-cancer effect is demonstrated in vitro while there was minimal or no effect on normal cell types. The survival of mice with intracranial implants of human malignant glioma cells was extended by direct injection of 2-5A-anti-hTR into the tumors.

7.1 MATERIALS AND METHODS
Oligonucleotide Synthesis and RT-PCR for Telomerase RNA.

Chimeric oligonucleotides were synthesised on solid supports and purified as described previously (Torrence et al 1993; Lesiak et al 1993; Xiao et al 1994, 1996; Cirino et al 1997). Tumor cells were seeded at 3×10$^5$ cells/well (3 ml) in 6-well plates and incubated overnight at 37° C. Cells were then treated with oligonucleotides (5 $\mu$M). Five hours later total RNA was isolated by using Trizol solution (GIBCO BRL, Grand Island, N.Y.). Expression of telomerase RNA was determined with RT-PCR. The RNA was reverse transcribed into complementary DNA (cDNA) with random oligos used as a primer, and then the cDNA was diluted three times with buffer 10×PCR buffer (Perkin-Elmer, Norwalk, Conn.) at a final concentration of 1:4. The DNA at each dilution was amplified using primers to antisense and sense sequences on opposite sides of the human telomerase RNA sequence, 5'-TTTGTCTAACCCTAACTGAGAAGG-3' (SEQ ID NO:4) and 5'TGTGAGCCGAGTCCTGGGTGCACG-3' (SEQ ID NO:5), respectively, or to the GAPDH coding sequence, 5'-ACCACCATGGAGAAGGCTGG-3' (SEQ ID NO:5) and 5'CGTAGGACCCGATGTGACTC-3' (SEQ ID NO:7), respectively, producing DNA fragments of 400 bp for telomerase cDNA and 508 bp for the GAPDH cDNA, respectively. The PCR went for 30 cycles (94° C., 1 min; 55° C., 1 min; 72° C., 2 min) for telomerase and 30 cycles (94° C., 1 min; 60° C., 1 min; 74° C., 3 min) for GAPDH. The PCR products were analyzed by 1.2% agarose gel electrophoresis and ethidium bromide staining.

Cell viability assay

The cytotoxic effect of 2-5A activator antisense complexes on tumor cells was determined using the trypan blue dye exclusion assay. Tumor cells were seeded at 10$^4$ cells/well (0.1 ml) in 96-well flat-bottomed plates and incubated overnight at 37° C. Then, oligonucleotides (5 micromolar) in water were added into cells every 12 hr. On successive days the cells were harvested and 25% of the total was examined microscopically to determine the percentage of viable cells, another 25% was replated to continue treatment and the remaining 50% were used for the TRAP assay.

TUNEL assay

To further determine whether treatment with oligonucleotides induced apoptosis, tumor cells and tissues were stained by the terminal deoxynucleotidyl transferase (TdT)-mediated DUTP nick end labeling (TUNEL) technique using Apo-Tag kit (peroxidase conjugated) (Oncor Inc., Gaithersburg, Md.). The staining of apoptotic cells was done on U373MG cells. Oligonucleotides with lipofectamine was added to the cells every day. The final concentrations were 0.5 micromolar and 8 microgram/ml for oligo and lipofectamine, respectively. Pictures were taken after 3 days of treatment.

spA$_4$-anti-hTR treatment of U373 cells in the presence of Lipofectamine™

Cells (10,000/well) were seeded on 96 well tissue culture dishes, and treated every 24 hours. A 10× concentrated mixture of oligonucleotides plus lipofectamine in water was prepared containing 5 micromolar oligonucleotide and 80 microgram per ml lipofectamine™ (Gibco/BRL) and incubated for 10 min at room temperature. Media was removed from the cells, 10 microliters of the oligonucleotide/lipofectamine mixture was added directly to the cultured cells followed by 90 microliters of media plus serum. The media was changed with oligonucleotide/lipofectamine treatments every 24 h. Cells were passaged when the control cells reached confluency, and viable cells were counted after staining with Trypan Blue (GibcoBRL). The numbers of cells treated only with lipofectamine were used as the control to calculate percentages of cell survival or viability.

Subcutaneous in vivo treatments.

U251-MG and U373 MG tumor cells (1.0×10$^6$ cells in 0.1 ml serum free DMEM and 0.1 ml Matrigel) were injected subcutaneously into the right flank of 8–12 week-old female Balb/c nude mice (5 mice for each treatment group). Tumor growth was monitored using calipers every 2- or 3-days. Tumor volume (V) was calculated as (L×W$^2$)/2, where L=length (mm) and W=width (mm). Oligonucleotide treatment was initiated when the tumors reached an average tumor volume of 60–100 mm$^3$ (about four to five weeks after injection). Oligonucleotides (5 nmol/20 microliter sterile distilled water) were administered by injecting them directly into the tumor every 24 hr for 7–14 days. Some experiments included lipofectamine at 1 microliter per 20 microliters final volume of oligonucleotide solution. Mice were sacrificed by cervical dislocation the day after the final injection and the tumors were removed, frozen rapidly and 12 $\mu$m sections were prepared for histological studies. During all of these experiments, which were approved by the CCF Research Programs Committee, the animals were housed and handled in accordance with the National Institutes of Health guidelines.

RCC and A375 tumor cells (500,000 cells per tumor) were injected subcutaneously. The treatments, begun 8 days after tumor cell inoculation, was with 40 microliter of 25 micromolar SpA$_4$-anti-hTR plus 1 microliter (2 microgram) lipofectamine injected in each tumor every day.

Treatment of intracranial U373-MG tumors with 2-5A-anti-hTR .

To establish murine models with intracranial tumors of U373-MG human malignant glioma cells, Balb/c nude mice were used. Mice (8–12 week-old male) were anesthetized using ketamine (90 mg/kg) and xylazine (10 mg/kg) and placed in a stereotaxic frame (Lab Standard w/18 Degree Earbars, Stoelting, Wood Dale, Ill.). Inoculation of $5 \times 10^5$ tumor cells (10 microliter of a tumor cell suspension of $5 \times 10^7$/ml in serum free DMEM [0.5 ml] and matrigel [0.5 ml]) was performed transcranially using a 27-gauge stainless-steel needle and microliter syringe (Perfectum, Popper & Sons, Inc., New Hyde Park, N.Y.). The needle insertion was in the skull 1 mm anterior and .2 mm lateral to the bregma and the depth of insertion was 4 mm from the skull (the caudate nucleus). The needle was left in place for 3 min and then withdrawn slowly over another minute. Two weeks after inoculation of tumor cells, mice were deeply anesthetized with ketamine/xylazine, and sacrificed by transcardiac perfusion with 4% formaldehyde. The brains were then sliced to include the injection site, and 12 $\mu$m sections were made for histological analysis. To determine the effect of 2-5A-anti-hTR on intracranial tumors, spA4-anti-hTR (3 nmol/10 microliter distilled water/3 microliter Lipofectamine, three times) was injected intracranially into the tumors via the same coordinates three weeks after inoculation of tumor cells (on Days 21, 23, and 25).
Design of the antisense oligonucleotide.

For successful application of this antisense technology, it is essential to construct antisense oligonucleotides against an "open" part of the RNA molecule to ensure the maximum likelihood of achieving homologous binding. To determine the best target sequence, therefore, the telomerase RNA structure was analyzed using the MFOLD program (Salser 1978, Cold Spring Harbor Symp. Quant. Biol. 42:985–1002; Zuker 1989, Methods of Enzymology 180:262–288; Frier et al 1986, Proc. Natl. Acad. Sci. USA 83:9373–9377). The predicted structure of the telomerase RNA showed that this molecule had very tight secondary folding which would make the binding of small oligonucleotides difficult (FIG. 7). The most "open" part of the molecule is seen between residues 76 and 94, 20 nucleotides 3' of the telomerase template sequence. Therefore, the 2-5A antisense oligonucleotide we designed against the predicted loop comprising nucleotides 76–94. BLASTN searches of available databases for this nucleotide sequence only revealed homologies to the human hTR and a DNA sequence from *H. influenzae*. To investigate the effect of 2-5A antisense telomerase on malignant glioma cells, spA$_4$-anti-hTR were synthesized with complete homology to the targeted sequence, as well as three control oligonucleotides; spA$_2$-anti-hTR, spA$_4$-anti-(M6)hTR and spA$_4$-anti-(M3)hTR (Table 2).

TABLE 2

Nomenclature and sequences of oligonucleotides complementary to human telomerase RNA nucleotides 76 to 94

| Oligonucleotides | Sequence |
|---|---|
| spA$_4$-anti-hTR | Sp5'A(2'p5'A)$_3$-Bu$_2$-5'GCG CGG GGA (SEQ ID GCA AAA GCA C3'-3'T5'NO: 2) |
| spA$_2$-anti-hTR | Sp5'A2'p5'A$_2$p-[(Bu)p]$_2$-5'GCG (SEQ ID CGGGGA GCA AAA GCA C3'-3'T5'NO: 2) |
| spA$_4$-anti-(M6)hTR | Sp5'A(2'p5'A)$_3$-Bu$_2$-5'GC<u>C</u> CG<u>C</u> GG<u>T</u> GC<u>T</u> AA<u>T</u> GC<u>T</u> C3'-3'T5' |
| spA$_4$-anti-(M3)hTR | Sp5'A(2'p5'A)$_3$-Bu$_2$-5'GC<u>C</u> CG<u>G</u> GG<u>T</u> (SEQ ID GCA AA<u>T</u> GCA C3'-3'T5'NO: 2) |

Bu - butanediol linkers;
underline indicates mismatched nucleotides

To establish the contribution of the 2-5A moiety of the chimeras to the anti-telomerase effects, spA2-anti-hTR contains only two 2', 5'-linked adenylyl residues instead of the usual four (Table 2). Chains of three or more 2', 5'-linked adenylyl residues are absolutely required for RNase L activation, and so dimeric forms of 2-5A are inactive (reviewed in Zhou et al 1993, Cell 72:753–765). Another control oligonucleotide, spA4anti-(M6)hTR, contains functional tetrameric 2-5A, but there are six mismatched nucleotides in the antisense cassette of the chimera which would reduce or prevent binding with the telomerase RNA. Another oligonucleotide, spA$_4$-anti-(M3)hTR, has only three mismatched nucleotides. All three oligonucleotides contained stabilizing modifications at both termini. The 5' termini contain a thiophosphate to protect against phosphatase activity and the opposite termini contain a 3', 3' inverted linkage to inhibit 3' and 5' exonuclease activities (Lesiak et al. 1993, Bioconjugate Chem. 4:467–472; Xiao et al. 1994, Bioorganic & Med. Chem. Letters 4:2609–2614; Xiao et al. 1996, Antisense Nucleic Acid Drug Devel. 6:247–258; Cirino et al. 1997, Proc. Natl. Acad. Sci. USA 94:1937–1942).
Effect of antisense telomerase in vitro.

The strategy was to determine the effect of inactivating telomerase RNA on cell growth and malignancy, therefore the telomerase expression profile in a number of generally available glioma cell lines using the TRAP assay was first established. The results are shown in FIG. 2. Cell extracts which produce a ladder of extended oligonucleotides with increasing sizes indicate the presence of telomerase activity (see methods section). In this survey the four cell lines showing telomerase activity were all derived from malignant gliomas, whereas cells from normal astrocytes (PIN) and low grade astrocytomas (RTLGA) were apparently telomerase negative. This correlation was also established in cells from primary brain tumor tissue, with only malignant gliomas showing telomerase activity. For these studies, therefore, U251-MG cells were selected for antisense treatment because they had the highest level of telomerase activity.

Aliquots of U251-MG cells were treated with the "active" oligonucleotide and the two controls for 5 hours. RNA was then prepared from these cells and subjected to RT-PCR to detect telomerase RNA. GAPDH mRNA was used to demonstrate a lack of non-specific activity of these oligonucleotides in these cells. As seen in FIG. 3, cells treated with spA$_4$-anti-hTR had no detectable telomerase RNA after 5 hours treatment. In contrast, telomerase RNA (hTR) was present in cells treated with the control oligonucleotides; spA$_2$-anti-hTR and spA$_4$-anti-(M6)hTR. Thus, hTR could be selectively destroyed in U251-MG cells. Since the RT-PCR assay is not quantitative, it was not possible to assess whether treatment with the spA$_2$-anti-hTR , which has the fully complementary target sequence, had any antisense effect by itself (see below). From these experiments it was clear, however, that the specific action of spA$_4$-anti-hTR was dependent upon both functional 2-5A and a genuine antisense effect.

Knowing that hTR could be inactivated by the 2-5A antisense treatment, U251-MG cells were treated every 12 hours over a 14 day period with the same three oligonucleotides. Cell viability was assessed every 2 days and the results are shown in FIG. 4. 79% of the cells treated with spA$_4$-anti-hTR were killed over the 14 day period with a significant (50%) reduction in cell viability after only 5 days. Cells treated with the mismatch control oligo showed little, if any, cell death over the treatment period. The spA$_2$-anti-hTR oligo showed a mild antisense effect although 80% of cells remained viable over the treatment period. These experiments have since been repeated on a number of occasions with U251-MG cells to test new batches of oligonucleotides, always with the same results. When other human malignant glioma cells (U373-MG, GB-1, and T98G) which express high levels of telomerase (FIG. 2), were treated with spA$_4$-anti-hTR, similar results were obtained (see below). Thus, after 14 days from the initial treatment with spA$_4$-anti-hTR, the viability of U251-MG cells, as shown by Trypan-blue exclusion assays, was suppressed in all cases. When cells treated with spA$_4$-anti-hTR were fixed and subjected to the TUNEL assay, an increased number of darkly staining nuclei indicating apoptotic cell death was detected. These experiments clearly demonstrated that treating cells with spA$_4$-anti-hTR inhibits telomerase activity and results in tumor cell death.

SpA$_4$-anti-hTR has a broad-specificity effect against different types of tumor cells while having minimal or no effects on the viability of normal cells.

To determine whether the anti-telomerase oligonucleotides had any effect on cells which do not express telomerase activity, normal human astrocytes (PIN) were treated following the same protocol used for the tumor cells. The TRAP assay was used to confirm that PIN cells do not express telomerase activity (FIG. 2). The results of treating PIN cells compared with a series of other glioma cell lines are shown in FIG. 5. Treatment of normal astrocytes with SpA$_4$-anti-hTR resulted in only a mild (2–3%) reduction in cell viability compared with the dramatic effect seen in the other cell lines.

For the experiments described below, lipofectamine was used to enhance the uptake of the oligonucleotides into cells (Williams et al., 1996, Leukemia 10:12, 1980–1909). This protocol (Methods) resulted in about 10-fold increases in the anti-tumor cell effect of SpA$_4$-anti-hTR (tumor cell viability was substantially reduced with 0.5 micromolar of SpA$_4$-anti-hTR delivered once a day). Using this protocol for 8 days, SpA$_4$-anti-hTR reduced cell viability by 9% and 35% in the normal human lung cell line, WI 38, and in normal diploid human fibroblasts (MRC5), respectively, while causing a 90% reduction in the viability of U373 cells.

To demonstrate the specificity of SpA$_4$-anti-hTR for tumor cells, effects were compared between a panel of different human tumor cell types. The viability of a renal cell carcinoma cell line, RCC, was shown to be reduced by 61% in three days by this protocol, whereas the control oligonucleotides, SpA$_2$-anti-hTR and SpA$_4$-(M6)-anti-hTR showed no reduction in viability after 3 days (FIG. 13). Similarly, the viability of the breast cancer cell line, MDA468, was reduced by 64% by SpA$_4$-anti-hTR, while the control oligonucleotides reduced cell viability by <20% (FIG. 6). Viability of the human melanoma cell line, A375, was reduced by 43% in three days by SpA$_4$-anti-hTR, while the control oligonucleotides had no effect (FIG. 7). There was <0.1 % survival of a second human melanoma cell line, SK-MEL-2, in response to SpA$_4$-anti-hTR, however a nonspecific, but reduced effect of the control oligonucleotides was observed in these cells (FIG. 8). Viability of a third human melanoma cell line, SK-MEL-5, was reduced by 43% by SpA$_4$-anti-hTR, with minimal effects by the control oligonucleotides (FIG. 7). Two prostate tumor cells lines, PC3 and DU145, were suppressed by SpA$_4$-anti-hTR treatments by 45% and 60%, respectively (FIGS. 6 and 10). The control oligonucleotides were relatively inactive on the PC3 cells, but had partial activity in the DU145 cells. The viability of the malignant glioma cell line, U373, was reduced by about 60% in 3 days, with intermediate effects by the control oligonucleotides (FIG. 6). Therefore, the proliferation and survival of every tumor cell type tested was inhibited by SpA$_4$-anti-hTR. Treatment of the U373 cells resulted in a time-dependent increase in apoptotic cells as determined by a TUNEL assay for DNA breakage (FIG. 11). After treating U373 cells for 3 days with SpA$_4$-anti-hTR plus lipofectamine, apoptosis was clearly visible (FIG. 12 lower panel). In contrast, there was no apoptosis detected in the control cells treated with lipofectamine without oligonucleotide (FIG. 12 upper panel).

The tumoricidal activity of spA$_4$-anti-hTR is a hybridization-dependent, antisense effect.

To further demonstrate that the anti-tumor cell effect of spA4-anti-hTR is hybridization-dependent, i.e. a genuine antisense effect, a derivative of spA$_4$-anti-hTR was synthesized with three mismatches, instead of the usual six mismatches (spA$_4$(M3)anti-hTR (Table 2). Daily treatments of U373 cells for 7 days with 0.5 micromolar concentrations of oligonucleotide in the presence of lipofectamine were done. In two separate cultures, spA$_4$-anti-hTR reduced cell viability to <2%. spA$_4$-(M3)anti-hTR, with three mismatches, reduced cell viability by 76%, while spA$_4$-(M6)anti-hTR, with 6 mismatches reduced viability by 43% and the defective 2-5A control, spA$_2$-anti-hTR, reduced viable cell numbers by 42%. Therefore, the effect of spA$_4$-(M3)anti-hTR was intermediate between that of spA$_4$-anti-hTR and spA$_4$-(M6)anti-hTR as expected for a hybridization-dependent mechanism.

Effect of 2-5A-anti-hTR in vivo against subcutaneous implants of human malignant glioma cells.

The effect of treating tumors which had been induced subcutaneously in nude mice with spA$_4$-anti-hTR was investigated, in these experiments both U251-MG and U373-MG cells were used. In the initial studies tumors were not consistently established in the flanks of nude mice by simple injection of these cell lines. However, when mixed with matrigel, tumors arose at 100% of the inoculated sites. Consequently all tumors in this treatment protocol were established in the presence of matrigel. Initially, five tumors were injected directly with either spA$_4$-anti-hTR or spA$_4$-anti-(M6)hTR oligonucleotides every 24 hours for 7 days. Prior to treatment, the two oligonucleotides were coded and only decoded after the final treatment and excision of the tumors. As shown in FIG. 13A, spA$_4$-anti-hTR significantly suppressed the growth of U251-MG and U373-MG tumors when compared with spA$_4$anti-(M6)hTR treatments (P<0.03 and P<0.01, respectively). In the animals treated with spA$_4$-anti-hTR, the mean tumor volume after the 7 day treatment was 36.55.9 and 73.328.1 mm³, for U251-MG or U373-MG cells respectively. In contrast, mean tumor volume reached 148.537.3 or 287.646.5 mm³ in control (spA$_4$-anti-(M6)hTR treated) animals. As predicted from the in vitro results, many apoptotic cells were observed in tumors treated with spA$_4$-anti-hTR, although tumors treated with spA$_4$-anti-(M6)hTR also showed a few apoptotic cells (FIG. 14). These observations were repeated and extended in a second series of experiments where the U251-MG tumors were treated for 14 days instead of 7 days (FIG. 13B). The same effect of the oligonucleotides was essentially found. Tumors treated with spA$_4$-anti-hTR showed an overall 48% reduction in their size during the treatment period whereas tumors treated with spA$_4$-anti-(M6)hTR showed a 87% increase in their size. These observations were confirmed by comparing the average net weight of the tumors in each group after treatment (54.0±28.7 mg for spA$_4$-anti-hTR, and 92.0+14.7 mg for spA$_4$-anti-(M6)hTR). In this second series of experiments, spA$_2$-anti-hTR was also included which mimicked the lack of response seen with spA$_4$-anti-(M6)hTR. The group of tumors treated with distilled water alone achieved a larger mean volume than any of the groups treated with oligonucleotides suggesting a possible non-specific effect with spA$_2$-anti-hTR and spA4-anti-(M6)hTR, although the mean net weight of the tumors from these groups was not significantly different. Interestingly, in the group of animals treated with spA$_4$-anti-hTR the tumors showed only a marginal additional reduction in size during days 8–14 of the treatment compared with the considerable effect seen in the first 7 days.

The effects of spA$_4$-anti-hTR combined with lipofectamine on tumor growth was determined with a renal cell carcinoma cell line, RCC, and the melanoma cell line, A375 (FIGS. 15). In the case of the RCC cells, tumor size increased by only 14% over a seven day period, during which time the control tumors, injected with lipofectamine alone, increased in size by 59% (FIG. 15). Similarly, the spA$_4$-anti-hTR treated A375 breast cancer tumor increased in size by only 17% in seven days while the control tumor increased in size by 61% (FIG. 16). These results show the anti-tumor effects of using spA$_4$-anti-hTR together with lipofectamine in vivo, while at the same demonstrating a broad-specificity anti-tumor effect.

Effect of intracranial treatments of malignant gliomas in nude mice on survival.

To determine the effect of spA$_4$-anti-hTR treatments on survival of mice from malignant gliomas in brain tissue, U373 cells were inoculated intracranially in nude mice. To ascertain that tumor formation was occurring, four mice were sacrificed after two-weeks and examined. Tumors infiltrating into surrounding normal tissues were clearly detected (FIG. 16A). All of untreated mice with intracranial U373-MG tumors died of their tumors within 6–7 weeks after intracranial inoculation of tumor cells (FIG. 16B). There was no significant difference between the sizes of intracranial tumors in mice. After three weeks of tumor cell growth, the mice received direct intracranial injections of spA$_4$-anti-hTR plus lipofectamine. All of the control mice died by 49 days after inoculation with the tumor cells (FIG. 16B). In contrast, treatment of mice bearing intracranial U373-MG tumors with spA4-anti-hTR was therapeutically effective resulting in 50% survival 9 weeks after inoculation of tumor cells (P<0.05). These results clearly demonstrate that spA$_4$-anti-hTR can be effectively delivered to the intracranial 373-MG tumors in nude mice, and the treatment modality with 2-5A-anti-hTR was effective for the treatment of intracranial malignant gliomas in this model.

Combination therapy with cisplatin.

To determine if the anti-malignant glioma cell activity of chemotherapeutic agent, cisplatin, could be enhance with SpA$_4$-anti-hTR, a combination therapy protocol was devised (FIG. 17). The point at which 50% cell death was achieved was using 1 microgram per ml of cisplatin plus 0.5 micromolar of SpA$_4$-anti-hTR; whereas in the absence of SpA$_4$-anti-hTR, >10 micrograms per ml of cisplatin were required to achieve 50% cell death (FIG. 17). These results suggest the possibility of combination therapies with SpA$_4$-anti-hTR and chemotherapeutic agents, such as cisplatin. Furthermore, we determined the effect of combining 2-5A-anti-hTR with cisplatin on U373-MG cells in vitro and in vivo. As shown in FIG. 17A, treatment with spA$_4$-anti-hTR increased the susceptibility of U373-MG cells to cisplatin. The IC$_{50}$ of cisplatin was reduced from 10.0 to 1.0 μg/ml by combination of spA$_4$-anti-hTR. The cytotoxic effect of cisplatin on subcutaneous tumors was significantly enhanced by combination with spA4-anti-hTR (P<0.01 or P<0.03 for cisplatin alone 1 or 5 mg/kg, respectively) (FIG. 17B). These results demonstrate that treatment with spA$_4$-anti-hTR may provide another means of chemosensitisation for malignant gliomas which are resistant to anticancer drugs.

Enhanced Anti-Tumor Cell Activity of SpA$_{12}$-anti-hTR

To determine the effect of extending the 2-5A moiety of 2-5A-anti-hTR, we have synthesized the following compound containing twelve 2',5'-linked adenylyl residues:

spA$_{12}$-anti-hTR Sp5'A(2'p5'A)$_{11}$-Bu$_2$-5'GCG CGG GGA GCA AAA GCA C3'-3'T5' (SEQ ID NO:2)

spA$_{12}$-anti-hTR or spA$_4$-anti-hTR, each at 0.5 micromolar, were mixed with lipofectamine and added daily to the U373 Cells (FIG. 18). While both compounds had similar activities at 4 days, there was considerably more anti-cellular activity of the spA$_{12}$-anti-hTR after 7 days of treatment. These data suggest that by extending the length of the 2-5A part of the chimeric oligonucleotide substantially increases activity.

These results clearly demonstrate that SpA$_4$-anti-hTR is effective in suppressing the growth and survival of a wide range of different human tumor cell types, both in vitro and in vivo in the nude mouse model. In contrast, telomerase negative, normal cells are relatively insensitive to the anti-cellular activities of SpA$_4$-anti-hTR. Furthermore, SpA$_4$-anti-hTR was able to enhance survival of mice with intracranial malignant gliomas after direct injection of the oligonucleotide mixed with lipofectamine. This strategy represents a novel protocol for the treatment of malignant glioma.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated herein by reference for all purposes.

We claim:

1. An activator-antisense complex comprising:
   a) an antisense oligonucleotide, having a hydroxyl moiety at a first end, which oligonucleotide is complementary to a portion of a RNA component of human telomerase predicted to have an open loop structure;
   b) a linker attached to the first end; and
   c) an activator of RNase L attached to the linker.

2. The complex of claim 1, wherein the sequence of the oligonucleotide is complementary to nucleotides 80 to 90 of SEQ ID NO: 1.

3. The complex of claim 1, wherein the oligonucleotide is complementary to between 15 and 20 nucleotides of the RNA portion of human telomerase.

4. The complex of claim 3, in which the oligonucleotide comprises the sequence of
   5' GCG CGG GGA GCA AAA GCA C 3' (SEQ ID NO: 2).

5. The complex of claim 4, in which the oligonucleotide activator is selected from the group consisting of sp5'A2'(p5'A2')$_2$-O-, sp5'A2'(p5'A2')$_3$-O-, p5'A2(p5'A2')$_2$-O-, and p5'A2 (p5'A2')$_3$-O-.

6. The complex of claim 1, in which the oligonucleotide activator is selected from the group consisting of sp5'A2'(p5'A2')$_2$-O-, sp5'A2'(p5'A2')$_3$-O-, p5'A2'(p5'A2')$_2$-O-, and p5'A2'(p5'A2')$_3$-O-.

7. The complex of claim 1, in which the first end is the 5' terminus, and the 3' terminal hydroxyl of the oligonucleotide is blocked by a blocker selected from the group consisting of a -p3'N5' nucleotide, a p-O-alkylamine, a p-O-hydroxyalkylamine, a sp-O-alkylamine, a sp-O-hydroxyalkylamine, ethyl and methyl.

8. The complex of claim 1, in which the first end is the 3' terminus.

9. The complex of claim 1, in which the oligonucleotide contains one or more phospho-moieties selected from the group consisting of phosphorothioate, methylphosphonate and methylphosphonothioate.

10. The complex of claim 1, in which the oligonucleotide contains at least one 2'O-methyl nucleotide.

11. A composition which comprises a concentration of the complex of claim 1 effective to inhibit telomerase activity in a mammalian cell and a pharmaceutically acceptable carrier.

12. A method of treating a telomerase-expressing, malignant disease in a subject which comprises administering to the subject a complex comprising:
   a) an oligonucleotide complementary to a portion of human telomerase RNA between 12 and 25 nucleotides;
   b) a linker attached to the oligonucleotide; and
   c) an activator of RNase L attached to the linker,
in a concentration effective to inhibit telomerase activity in a cell or tumor of said malignant disease.

13. The method of claim 12, in which the sequence of said oligonucleotide is complementary to a portion of human telomerase RNA of between 12 and 25 nucleotides, which portion contains a sequence of nucleotides 80 through 90 of SEQ ID NO: 1.

14. The method of claim 12, wherein the sequence of the oligonucleotide comprises the sequence of
   5' GCG CCG GGA GCA AAA GCA C 3' (SEQ ID NO: 2).

15. The method of claim 12, wherein the oligonucleotide is complementary to between 15 and 20 nucleotides of the RNA portion of human telomerase.

16. The method of claim 15, wherein the oligonucleotide has the sequence of SEQ ID NO: 2.

17. The method of claim 12 which further comprises administering a chemotherapeutic agent in combination with the complex.

18. The method of claim 17, in which the chemotherapeutic agent is selected from the group comprising: cisplatin, doxorubicin, mitomycin, daunorubicin, bleomycin, actinomycin D or neocarzinostatin.

19. A method of inhibiting the growth of a telomerase expressing malignant cell or tumor which comprises a step of administering a composition comprising an activator antisense complex, which complex comprises:
   a) an oligonucleotide complementary to an open loop structure;
   b) a linker attached to the first end; and
   c) an activator of RNase L attached to the linker; and
   d) a pharmaceutically acceptable carrier,
in a concentration effective to inhibit telomerase activity in said telomerase expressing malignant cell or tumor.

20. The method of claim 19, in which the sequence of said oligonucleotide is complementary to a portion of human telomerase RNA of between 12 and 25 nucleotides.

21. The method of claim 20, wherein the sequence of said oligonucleotide comprises the sequence of
   5' GCG CGG GGA GCA AAA GCA C 3'(SEQ. ID NO: 2).

22. The method of claim 19, wherein said oligonucleotide is complementary to between 15 and 20 nucleotides of the RNA portion of human telomerase.

23. The method of claim 19, which further comprises administering a chemotherapeutic agent.

24. The method of claim 19 in which the malignant cell or tumor is selected from the group consisting of: brain tumor malignant glioma, breast tumor, renal cell cancer, melanoma or prostate cancer.

25. The method of claim 19 in which further comprises administering a chemotherapeutic agent in combination with the activator oligonucleotide complex.

26. The method of claim 25 in which the chemotherapeutic agent is selected from the group comprising: cisplatin, doxorubicin, mitomycin, daunorubicin, bleomycin, actinomycin D or neocarzinostatin.

27. The complex of claim 1 wherein the oligonucleotide is complementary to the open loop structure extending from nucleotides 109 to 113.

28. The complex of claim 1 wherein the oligonucleotide is complementary to the open loop structure extending from nucleotides 150 to 163.

29. The complex of claim 1 wherein the oligonucleotide is complementary to the open loop structure extending from nucleotides 267 to 272.

* * * * *

SEQUENCE LISTING

<160> NUMBER OF SEQ ID NOS: 9

<210> SEQ ID NO 1
<211> LENGTH: 962
<212> TYPE: RNA
<213> ORGANISM: Homo sapiens -continued

```
<400> SEQUENCE: 1
ggguugcgga ggguggggccu gggaggggug guggccauuu uuugucuaac ccuaacugag      60
aagggcguag gcgccgugcu uuugcuccccc gcgcgcuguu uuucucgcug acuuucagcg     120
ggcggaaaag ccucggccug ccgccuucca ccguucauuc uagagcaaac aaaaaaugu       180 agcugcuggc ccguucgccu cccggggacc ugcggcgggu cgccugccca gcccccgaac      240
cccgccugga gccgcggucg gccgggggcu ucuccggagg cacccacugc caccgcgaag     300
aguugggcuc ugucagccgc gggucucucg ggggcgaggg cgagguucac cguuucaggc     360
cgcaggaaga ggaacggagc gaguccccgcc gcggcgcgau ucccugagcu gugggacgug    420
cacccaggac ucggcucaca caugcaguuc gcuuccugu ugguggggg aacgccgauc       480 gugcgcaucc gucaccccuc gccggcagug ggggcuugug aaccccccaaa ccugacugac     540 ugggccagug ugcugcaaau uggcaggaga cgugaaggca ccuccaaagu cggccaaaau    600
gaaugggcag ugagccgggg uugccuggag ccguuccugc gugggguucuc ccgucuuccg   660 cuuuuuguug ccuuuuaugg uuguauuaca acuuaguucc ugcucugcag auuuuguuga    720 ggguuuuugcu ucucccaagg uagaucucga ccaguccccuc aacggggugu ggggagaaca  780
gucauuuuuu uuugagagau cauuuaacau uuaaugaaua uuuaauuaga agaucuaaau    840
gaacauugga aauuguguuc cuuuaauggu caucgguuua ugccagaggu uagaaguuuc    900
uuuuuugaaa aauuagaccu uggcgaugac cuugagcagu aggauauaac ccccacaagc    960
uu                                                                     962

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gcgcggggag caaaagcac                                                   19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gcccgcggtg ctaatgctc                                                   19

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
tttgtctaac cctaactgag aagg                                             24

<210> SEQ ID NO 5
<211> LENGTH: 24
<212> TYPE: DNA
<213> ORGANISM: Artificial Sequence
```

-continued

```
<220> FEATURE:
<223> OTHER INFORMATION: Description of Artificial Sequence: primer

<400> SEQUENCE: 5
tgtgagccga gtcctgggtg cacg                                              24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
accaccatgg agaaggctgg                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 7
cgtaggaccc gatgtgactc                                                   20

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gcgcggggaa aagcac                                                       16

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gcccggggtg caaatgcac                                                    19
```